(12) United States Patent
Bäumler et al.

(10) Patent No.: US 9,302,004 B2
(45) Date of Patent: Apr. 5, 2016

(54) PHENALENE-1-ONE DERIVATIVES, METHOD FOR PRODUCING SAME AND USE THEREOF

(75) Inventors: Wolfgang Bäumler, Langquaid (DE); Ariane Felgenträger, Regensburg (DE); Karin Lehner, Hall in Tirol (AT); Tim Maisch, Nürnberg (DE); Johannes Regensburger, Barbing (DE); Francesco Santarelli, Köln (DE); Andreas Späth, Regensburg (DE)

(73) Assignee: TRIOPTOTEC GMBH (DE)

( * ) Notice: Subject to any disclaimer, the term of this patent is extended or adjusted under 35 U.S.C. 154(b) by 63 days.

(21) Appl. No.: 14/001,145

(22) PCT Filed: Feb. 23, 2012

(86) PCT No.: PCT/EP2012/053062
§ 371 (c)(1),
(2), (4) Date: Oct. 22, 2013

(87) PCT Pub. No.: WO2012/113860
PCT Pub. Date: Aug. 30, 2012

(65) Prior Publication Data
US 2014/0039184 A1  Feb. 6, 2014

(30) Foreign Application Priority Data

Feb. 24, 2011 (DE) .......................... 10 2011 012 343

(51) Int. Cl.
*C07D 265/30* (2006.01)
*A61K 41/00* (2006.01)
*A61K 31/137* (2006.01)
*A61K 31/14* (2006.01)
*A61K 31/4425* (2006.01)
*C07C 45/75* (2006.01)
*C07C 217/10* (2006.01)
*C07C 225/16* (2006.01)
*C07C 271/16* (2006.01)
*C07C 271/20* (2006.01)
*C07C 279/10* (2006.01)
(Continued)

(52) U.S. Cl.
CPC .............. *A61K 41/0057* (2013.01); *A61K 8/41* (2013.01); *A61K 8/416* (2013.01); *A61K 8/43* (2013.01); *A61K 8/494* (2013.01); *A61K 8/4913* (2013.01); *A61K 8/4953* (2013.01); *A61K 31/137* (2013.01); *A61K 31/14* (2013.01); *A61K 31/4425* (2013.01); *A61Q 11/02* (2013.01); *C07C 45/75* (2013.01); *C07C 217/10* (2013.01); *C07C 225/16* (2013.01); *C07C 271/16* (2013.01); *C07C 271/20* (2013.01); *C07C 279/10* (2013.01); *C07C 279/12* (2013.01); *C07C 279/24* (2013.01); *C07D 211/58* (2013.01); *C07D 213/20* (2013.01); *C07D 295/116* (2013.01); *A61K 2800/81* (2013.01); *A61L 2/088* (2013.01); *A61L 2/10* (2013.01); *C07C 2103/28* (2013.01)

(58) Field of Classification Search
CPC ............. C07D 295/023; C07D 265/30; C07D 295/027; C07D 213/74; C07C 213/02
USPC .................................................. 544/106, 155
See application file for complete search history.

(56) References Cited

U.S. PATENT DOCUMENTS

2007/0110672 A1* 5/2007 Bellott ............... A61K 49/0021
424/9.6

FOREIGN PATENT DOCUMENTS

DE  22 24 371 A1  1/1973
EP  0 341 018 A1  11/1989
(Continued)

OTHER PUBLICATIONS

Flors, C., Nonell, S., "Light and Singlet Oxygen in plant Defense Against Pathogens: Phototoxic Phenalenone Phytoalexins", Accounts of Chemical Research, May 1, 2006, 39 (5), pp. 293-300.*
(Continued)

*Primary Examiner* — Nyeemah A Grazier
*Assistant Examiner* — Sagar Patel
(74) *Attorney, Agent, or Firm* — Ostrolenk Faber LLP

(57) ABSTRACT

The present disclosure relates to a compound of formula (1):

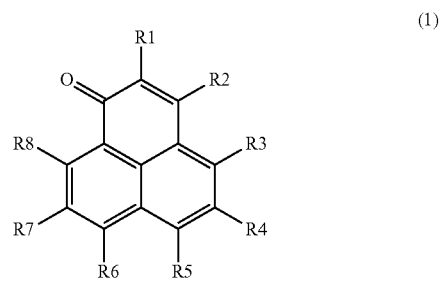

where R1 through R8, which can be identical or different from each other, each are selected from of the group comprising hydrogen and the radical $-(CH_2)_k-X$, where k is a whole number from 1 to 20 and where X is an organic radical comprising a) at least one neutral, protonizable nitrogen atom and/or b) at least one positively charged nitrogen atom, under the provision that at least 1 radical R1 through R8 is not hydrogen. The invention further relates to the production and use of said compound.

12 Claims, 5 Drawing Sheets

(51) Int. Cl.

| | |
|---|---|
| *C07C 279/12* | (2006.01) |
| *C07C 279/24* | (2006.01) |
| *C07D 211/58* | (2006.01) |
| *C07D 213/20* | (2006.01) |
| *C07D 295/116* | (2006.01) |
| *A61K 8/41* | (2006.01) |
| *A61K 8/43* | (2006.01) |
| *A61K 8/49* | (2006.01) |
| *A61Q 11/02* | (2006.01) |
| *A61L 2/08* | (2006.01) |
| *A61L 2/10* | (2006.01) |

(56) References Cited

FOREIGN PATENT DOCUMENTS

| GB | 1 394 672 | 5/1975 |
|---|---|---|
| GB | 2 337 530 | 11/1999 |

OTHER PUBLICATIONS

International Search Report and Written Opinion dated Aug. 27, 2012 issued in corresponding International patent application No. PCT/EP2012/053062.

German Search Report dated Feb. 8, 2012 issued in corresponding German patent application No. 10 2011 012 343.1.

Boyce, J. M. and Pittet, D.: "Guidelines for hand hygiene in healthcare settings. Recommendations of the Healthcare Infection Control practices Advisory Committee and the HIPAC/SHEA/APIC/IDSA Hand Hygiene Task Force", Am. J. Infect. Control 30 (8), 2002, pp. 1-46 and Infect Control Hosp. Epidemiol. 23, pp. 3-40.

DIN EN 14885: Jan. 2007 "Chemische Desinfektionsmittel und Antiseptika—Anwendung Europäischer Normen für chemische Desinfektionsmittel und Antiseptika".

Radenau, H. F. und Schwebke, I.: "Leitlinie der Deutschen Vereinigung zur Bekämpfung der Viruskrankheiten (DVV) e. V. und des Robert-Koch-Instituts (RKI) zur Prüfung von chemischen Desinfektionsmitteln auf Wirksamkeit gegen Viren in der Humanmedizin" Bundesgesundheitsblatt, Gesundheitsforschung Gesundheitsschutz 51 (8), (2008), pp. 937-945 (with English translation).

Christina Flors et al.: "Light and Singlet Oxygen in Plant Defense Against Pathogens: Phototoxic Phenalenone Phytoalexins +", Accounts of Chemical Research, Bd. 39, Nr. 5, May 1, 2006, pp. 293-300.

Nasser K. Thallaj et al.: "The Design of Metal Chelates with a Biologically Related Redox-Active Part: Bonjugation of Riboflavin to Bis(2-pyridylmethy_amine Ligand and Preparation of a Ferric complex", European Journal of Inorganic Chemistry, Bd. 2007, Nr. 1, pp. 44-47.

Michael R. Detty et al.: "Current Clinical and Prelinical Photosensitizers for Use in Photodynamic Therapy", Journal of Medicinal Chemistry, Bd. 47, Nr. 16, Jul. 1, 2004, pp. 3897-3915.

Esther Oliveros et al.: "Photochemistry of the singlet oxygen [$O_2(^1\Delta g)$] sensitizer perinaphthenone (phenalenone) in N, N'-dimethylacetamide and 1,4-dioxane", New Journal of Chemistry, Bd. 23, Nr. 1, Jan. 1, 1999, pp. 85-93.

* cited by examiner

A)

B)

A)

B)

A)

B)

A)

B)

A)

B)

PHENALENE-1-ONE DERIVATIVES, METHOD FOR PRODUCING SAME AND USE THEREOF

CROSS REFERENCE TO RELATED APPLICATIONS

The present application is a 35 U.S.C. §371 National Phase conversion of PCT/EP2012/053062, filed Feb. 23, 2012, which claims benefit of German Application No. 10 2011 012 343.1, filed Feb. 24, 2011, the disclosure of which is incorporated herein by reference. The PCT International Application was published in the German language.

BACKGROUND OF THE INVENTION

The present invention relates to 1H-phenalene-1-one derivatives, and the production and use thereof.

The active or passive penetration, adhesion and multiplication of pathogens in a host is called infection. Sources for infectious particles occur everywhere. Thus, for example, the human body is colonized by a large number of microorganisms which, as a rule, are kept under control by the normal metabolism and a sound immune system. However, for example if the immune system is weakened, a proliferation of the pathogens and, depending on the type of pathogenic agent, different symptoms can result. Doctors hold ready specific antagonists for many diseases caused by pathogenic agents, for example antibiotics to counter bacteria or antimycotics to counter fungi or virostatics to counter viruses. However, with the use of these antagonists, the occurrence of resistant pathogens, which sometimes have resistance to several antagonists at the same time, is increasingly to be observed. The treatment of infectious diseases has become increasingly difficult because of the occurrence of these resistant or multi-resistant pathogens. The clinical consequence of resistance is manifested by a failure of the treatment, above all in immunosuppressed patients.

New starting points for the fight against resistant or multi-resistant germs are therefore firstly the search for new antagonists, for example antibiotics or antimycotics, and secondly the search for alternative inactivation possibilities.

Photodynamic inactivation of microorganisms has proved its worth as an alternative method. Two different photo-oxidative processes play a decisive role in the photodynamic inactivation of microorganisms. On the one hand, the presence of a sufficient quantity of oxygen and, on the other hand, the localization of a so-called photosensitizer which is excited by light of a corresponding wavelength are prerequisites for the progress of a photo-oxidative inactivation. The excited photosensitizer can bring about the formation of reactive oxygen species (ROS), wherein on the one hand radicals, for example superoxide anions, hydrogen peroxide or hydroxyl radicals, and/or on the other hand excited molecular oxygen, for example singlet oxygen, can be formed.

In both reactions, the photo-oxidation of specific biomolecules which are located in direct proximity of the reactive oxygen species (ROS) is of primary importance. In particular an oxidation of lipids and proteins which occur for example as constituents of the cell membrane of microorganisms takes place. The destruction of the cell membrane in turn results in the inactivation of the microorganisms concerned. A similar elimination process is adopted for viruses and fungi.

For example, all molecules are attacked by singlet oxygen. However, unsaturated fatty acids in the membranes of bacteria are particularly susceptible to damage. Healthy cells belonging to the body have a cellular defense against attacks by free radicals, so-called catalases or superoxide dismutases. Healthy cells belonging to the body can therefore counteract damage by reactive oxygen species (ROS), for example radicals or singlet oxygen.

Numerous photosensitizers are known from the state of the art which originate for example from the group of porphyrins and derivatives thereof or phthalocyanines and derivatives thereof or fullerenes and derivatives thereof or derivatives with phenothiazinium structure, such as for example methylene blue or toluidine blue, or representatives of the phenoxazinium series, such as for example Nile blue. The photodynamics of methylene blue or toluidine blue against bacteria are already used for example in dentistry.

The photosensitizers known from the state of the art are usually substances with a relatively complex molecular structure and therefore expensive production methods.

It is known that 1H-phenalene-1-one and sulfonated 1H-phenalene-1-one have high yields of singlet oxygen, wherein however the affinity to microorganisms is low. It is furthermore known that singlet oxygen can diffuse only over a small distance before it reacts or is disintegrated. The inactivation of microorganisms by 1H-phenalene-1-one and sulfonated 1H-phenalene-1-one is therefore insufficient.

Hair-coloring compositions based on phenalenone derivatives are known from GB 2 337 530 A in which the ring carbon atoms can be directly substituted by an aminodialkyl group.

An object of the present invention is therefore to provide novel photosensitizers which inactivate microorganisms more efficiently.

SUMMARY OF THE INVENTION

The object of the present invention is achieved by the provision of a compound with Formula (1):

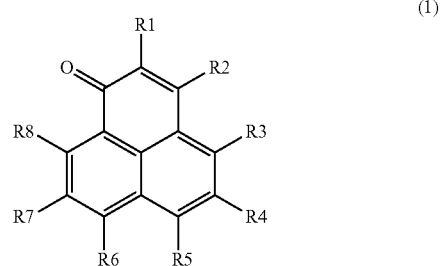

wherein R1 to R8, which can in each case be the same or independently of each other different, are in each case selected from the group which consists of hydrogen and the radical —$(CH_2)_k$—X, wherein k is an integer from 1 to 20, preferably from 1 to 19, preferably from 1 to 17, further preferably from 1 to 13, further preferably from 1 to 9, further preferably from 1 to 6, further preferably from 1 to 4, further preferably is 1, and wherein X is an organic radical which contains a) at least one neutral, protonatable nitrogen atom and/or b) at least one positively charged nitrogen atom, with the proviso that at least 1 radical R1 to R8, preferably R1, is not hydrogen.

The compound according to the invention with Formula (1) is a 1H-phenalene-1-one derivative which is also called such in the following.

In addition, the object is achieved by the provision of a method for producing the compound according to Formula (1), wherein the method comprises the following steps:

(A1) reacting 1H-phenalene-1-one with at least one alkylating agent of the formula Y—(CH$_2$)$_h$—Z, wherein Y is selected from the group which consists of H, Cl, Br, I, p-toluene sulfonyl (OTs), methanesulfonyl (OMs), OH and alkyl$_2$S$^+$, preferably H, Cl, Br and I, wherein alkyl can be the same or independently of each other different and preferably means methyl, ethyl, propyl or butyl, optionally in the presence of a catalyst, preferably Lewis acid or Brønsted acid, obtaining a compound with Formula (58):

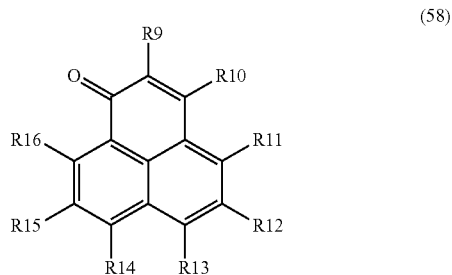

(58)

wherein R9 to R16, which can be the same or independently of each other different, mean in each case hydrogen or the radical —(CH$_2$)$_h$—Z, wherein h means an integer from 1 to 20, preferably from 1 to 19, preferably from 1 to 17, further preferably from 1 to 13, further preferably from 1 to 9, further preferably from 1 to 6, further preferably from 1 to 4, further preferably means 1, and wherein Z is selected from the group which consists of Cl, Br, I, OTs, OMs, OH and alkyl$_2$S$^+$, wherein alkyl can be the same or independently of each other different and preferably means methyl, ethyl, propyl or butyl, with the proviso that at least 1 radical R9 to R16, preferably R9, is not hydrogen, or (A2) reacting 1H-phenalene-1-one with formaldehyde and at least one halogen hydracid, optionally in the presence of a catalyst, obtaining a compound with Formula (58):

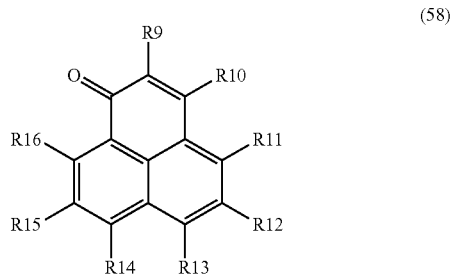

(58)

wherein R9 to R16, which can be the same or independently of each other different, mean in each case hydrogen or the radical —CH$_2$—W, and wherein W is selected from the group which consists of Cl, Br and I, with the proviso that at least 1 radical R9 to R16 is not hydrogen, (B) reacting the compound obtained in step (A1) or (A2) with Formula (58) with an organic compound which contains a) at least one neutral, protonatable nitrogen atom and/or b) at least one positively charged nitrogen atom, optionally in the presence of a base, and optionally (C) removing any amino protecting groups present, obtaining the 1H-phenalene-1-one derivative according to the invention of Formula (1).

The halogen hydracid used in step (A2) is preferably HCl, HBr, HI or mixtures thereof. HCl has proved to be a very suitable halogen hydracid. Preferably, in step (A2), the radical —CH$_2$—W is —CH$_2$—Cl.

The alkylating agent according to step (A2) is preferably produced in situ. Here, the radical R is introduced for example by chloromethylation, optionally with reagents such as phosphoric acid, hydrochloric acid and formaldehyde, at increased temperature. Furthermore, the object is achieved by the provision of a pharmaceutical composition containing at least one compound with Formula (1) or a pharmacologically compatible salt and/or ester and/or complex thereof, as well as by the provision of a coated object, the surface of which has at least one compound with Formula (1).

Furthermore, the object is achieved by the use of the compound with Formula (1) in the inactivation of microorganisms.

Further preferred embodiments of the present invention are described in the dependent claims.

BRIEF DESCRIPTION OF THE DRAWINGS

FIG. 1A) shows the results of incubation of *Staphylococcus aureus* samples with the compound obtained in Example 2 for 15 minutes.

FIG. 1B) shows the results of incubation of *Escherichia coli* samples with the compound obtained in Example 2 for 15 minutes.

FIG. 2A) shows the results of incubation of *Staphylococcus aureus* samples with the compound obtained in Example 10 for 15 minutes.

FIG. 2B) shows the results of incubation of *Escherichia coli* samples with the compound obtained in Example 10 for 15 minutes.

FIG. 3A) shows the results of incubation of *Staphylococcus aureus* samples with the compound obtained in Example 5b) for 15 minutes.

FIG. 3B) shows the results of incubation of *Escherichia coli* samples with the compound obtained in Example 5b) for 15 minutes.

FIG. 4A) shows the results of incubation *Staphylococcus aureus* samples with the compound obtained in Example 4b) for 15 minutes.

FIG. 4B) shows the results of incubation of *Escherichia coli* samples with the compound obtained in Example 4b) for 15 minutes.

FIG. 5A) shows the results of incubation of *Staphylococcus aureus* samples with the compound obtained in Example 7 for 15 minutes.

FIG. 5B) shows the results of incubation of *Escherichia coli* samples with the compound obtained in Example 7 for 15 minutes.

DESCRIPTION OF PREFERRED EMBODIMENTS

Figure 1:
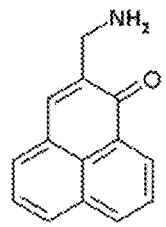
FIG. 1 shows the structural formula of the compound 2-aminomethyl-1H-phenalene-1-one obtained in Example 2.
Figure 1:
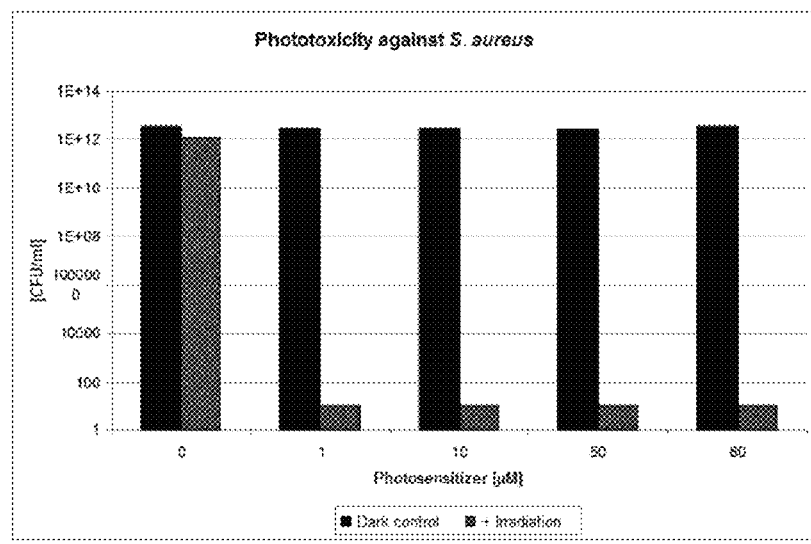
Figure 1:
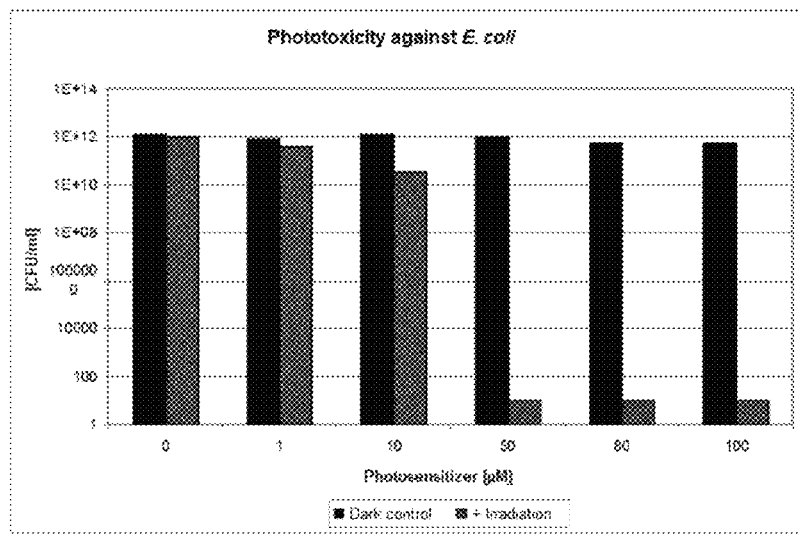

By "photosensitizers" are meant, according to the invention, compounds which absorb electromagnetic radiation, preferably visible light, UV light and/or infrared light, and then produce reactive oxygen species (ROS), preferably free radicals and/or singlet oxygen, from triplet oxygen.

By the term "photodynamic therapy" is meant, according to the invention, the light-induced inactivation of cells or microorganisms.

By the term "inactivation" is meant, according to the invention, the reduction of the viability or the destruction of a microorganism, preferably its destruction. A light-induced inactivation can be determined for example by reduction of the number of microorganisms after irradiation of a defined starting quantity of these microorganisms in the presence of at least one compound according to the invention with Formula (1).

According to the invention, by a reduction of the viability is meant that the number of microorganisms is reduced by at least 99.0%, preferably by at least 99.9%, further preferably by at least 99.99%, further preferably by at least 99.999%, still further preferably by at least 99.9999%. The number of microorganisms is extremely preferably reduced by more than 99.9 to 100%, preferably by more than 99.99 to 100%.

The reduction of the number of microorganisms is preferably indicated according to Boyce, J. M. and Pittet, D. ("Guidelines for hand hygiene in healthcare settings. Recommendations of the Healthcare Infection Control Practices Advisory Committee and the HIPAC/SHEA/APIC/IDSA Hand Hygiene Task Force", Am. J. Infect. Control 30 (8), 2002, pages 1-46) as a $\log_{10}$ reduction factor.

According to the invention, by the term "$\log_{10}$ reduction factor" is meant the difference between the common logarithm of the number of microorganisms before and the common logarithm of the number of microorganisms after an irradiation of these microorganisms with electromagnetic radiation in the presence of at least one compound according to the invention with Formula (1).

Suitable methods for determining the $\log_{10}$ reduction factor are described for example in DIN EN 14885:2007-01 "Chemical disinfectants and antiseptics—Application of European Standards for chemical disinfectants and antiseptics" or in Rabenau, H. F. and Schwebke, I. ("Leitlinie der Deutschen Vereinigung zur Bekämpfung der Viruskrankheiten (DVV) e.V und des Robert Koch-Instituts (RKI) zur Prüfung von chemischen Desinfektionsmitteln auf Wirksamkeit gegen Viren in der Humanmedizin" Bundesgesundheitsblatt, Gesundheitsforschung, Gesundheitsschutz 51(8), (2008), pages 937-945).

The $\log_{10}$ reduction factor after an irradiation of microorganisms with electromagnetic radiation in the presence of at least one compound according to the invention with Formula (1) is preferably at least 2 $\log_{10}$, preferably at least 3 $\log_{10}$, further preferably at least 4 $\log_{10}$, further preferably at least 4.5 $\log_{10}$, further preferably at least 5 $\log_{10}$, further preferably at least 6 $\log_{10}$, still further preferably at least 7 $\log_{10}$, still further preferably at least 7.5 $\log_{10}$.

For example, a reduction of the number of microorganisms after an irradiation of these microorganisms with electromagnetic radiation in the presence of at least one compound according to the invention with Formula (1) by 2 powers of ten, relative to the starting quantity of these microorganisms, means a $\log_{10}$ reduction factor of 2 $\log_{10}$.

Further preferably, the number of microorganisms after an irradiation of these microorganisms with electromagnetic radiation in the presence of at least one compound according to the invention with Formula (1) is reduced by at least 1 power of ten, further preferably by at least 2 powers of ten, preferably by at least 4 powers of ten, further preferably by at least 5 powers of ten, further preferably by at least 6 powers of ten, still further preferably by at least 7 powers of ten, in each case relative to the starting quantity of these microorganisms.

By the term "microorganisms" is meant within the meaning of the invention in particular viruses, archaea, prokaryotic microorganisms, such as bacteria and bacterial spores, and eukaryotic microorganisms, such as fungi, protozoa, fungal spores, single-celled algae. The microorganisms can occur as single-celled or multi-celled organisms, for example as fungus mycelium.

According to the invention, the 1H-phenalene-1-one derivative has Formula (1), wherein R1 to R8, which can in each case be the same or independently of each other different, are in each case selected from the group which consists of hydrogen and the radical —$(CH_2)_k$—X, wherein k is an integer from 1 to 20, preferably from 1 to 19, preferably from 1 to 17, further preferably from 1 to 13, further preferably from 1 to 9, further preferably from 1 to 6, further preferably from 1 to 4, further preferably is 1, wherein X is an organic radical which contains a) at least one neutral, protonatable nitrogen atom and/or b) at least one positively charged nitrogen atom, with the proviso that at least one radical R1 to R8, preferably R1, is not hydrogen.

In a further preferred embodiment of the compound with Formula (1), R2 to R8 are hydrogen and R1 is —$(CH_2)_k$—X, wherein k is an integer from 1 to 20, preferably from 1 to 19, preferably from 1 to 17, further preferably from 1 to 13, further preferably from 1 to 9, further preferably from 1 to 6, further preferably from 1 to 4, further preferably is 1, and wherein X is an organic radical which contains a) at least one neutral, protonatable nitrogen atom and/or b) at least one positively charged nitrogen atom [is selected].

Preferably, the organic radical X which contains a) at least one neutral, protonatable nitrogen atom and/or b) at least one positively charged nitrogen atom is selected from the group which consists of saturated or unsaturated alkyl radicals, saturated or unsaturated heteroalkyl radicals, saturated or unsaturated cycloalkyl radicals, saturated or unsaturated heterocyclic alkyl radicals, aryl radicals and heteroaryl radicals. The aryl radicals in each case preferably have at most 4, further preferably at most 3, further preferably at most 2, anellated rings. The aryl radicals still further preferably have 1 ring in each case. The heteroaryl radicals in each case preferably have at most 4, further preferably at most 3, further preferably at most 2, anellated rings. The heteroaryl radicals still further preferably have 1 ring in each case.

In a further preferred embodiment, the heteroaryl radicals in each case have 5 to 20, preferably 5 to 13, further preferably 5 to 7, ring atoms which comprise at least 1 carbon atom and 1 to 4 nitrogen atoms as well as optionally 1 or 2 oxygen or sulfur atoms. In a further preferred embodiment, the saturated or unsaturated heterocyclic alkyl radicals in each case have 5 to 20, preferably 5 to 13, further preferably 5 to 7, ring atoms which comprise at least 1 carbon atom and 1 to 4 nitrogen atoms as well as optionally 1 or 2 oxygen or sulfur atoms.

In a further preferred embodiment, the saturated or unsaturated alkyl radicals are in each case selected from the group which consists of methyl, ethyl, n-propyl, n-butyl, n-pentyl, n-hexyl, n-heptyl and n-octyl.

In a further preferred embodiment, the 1H-phenalene-1-one derivative according to the invention has a molecular weight of less than 1100 g/mol, preferably less than 990 g/mol, further preferably less than 810 g/mol, further preferably less than 690 g/mol, still further preferably less than 610 g/mol, still further preferably less than 600 g/mol, still further preferably less than 570 g/mol.

Unless otherwise indicated, chirality centers can be present in R or in S configuration. The invention relates to both the optically pure compounds and stereoisomer mixtures, such as enantiomer mixtures and diastereomer mixtures, in any ratio.

The invention preferably also relates to mesomers and/or tautomers of the compound with Formula (1), both the pure compounds and isomer mixtures in any ratio.

In a preferred embodiment, X is represented by Formula (2):

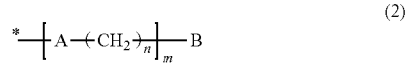
(2)

wherein A is an oxygen or a sulfur atom or a nitrogen atom which can be neutral or positively charged and wherein n is an integer from 1 to 8, preferably from 1 to 4, further preferably from 1 to 3, and m is an integer from 0 to 100, preferably from 0 to 10, and wherein B is selected from the group which consists of the radicals of Formulae (3), (4) and (5):

(3)

(4)

(5)

and wherein each of the radicals $R^{(I)}$, $R^{(II)}$ and $R^{(III)}$ independently of each other is selected from hydrogen, amidino, guanidino, monosaccharide or C1 to C20 alkyl, preferably C2 to C18 alkyl, which can be straight-chained or branched, preferably straight-chained, wherein the above-named alkyl radicals are unsubstituted or can be substituted with at least one radical which is selected from the group which consists of amino, methylamino, dimethylamino, trimethylammonio, imino, methylimino, amidino, hydroxy and guanidino.

Suitable monosaccharides preferably have 3 to 7 carbon atoms, preferably 5 to 6 carbon atoms, and have a carbonyl group, preferably aldehyde group or keto group, as well as at least one hydroxyl group and can be present open-chained or cyclic, preferably as furanose or pyranose.

Suitable monosaccharides are preferably selected from the group which consists of D-glycerol aldehyde, L-glycerol aldehyde, D-erythrose, L-erythrose, D-threose, L-threose, D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, dihydroxyacetone, D-erythrulose, L-erythrulose, D-ribulose, L-ribulose, D-xylulose, L-xylulose, D-psicose, L-psicose, D-fructose, L-fructose, D-sorbose, L-sorbose, D-tagatose and L-tagatose. Suitable monosaccharides are further preferably selected from the group which consists of D-ribose, L-ribose, D-arabinose, L-arabinose, D-xylose, L-xylose, D-lyxose, L-lyxose, D-allose, L-allose, D-altrose, L-altrose, D-glucose, L-glucose, D-mannose, L-mannose, D-gulose, L-gulose, D-idose, L-idose, D-galactose, L-galactose, D-talose, L-talose, D-ribulose, L-ribulose, D-xylulose, L-xylulose, D-psicose, L-psicose, D-fructose, L-fructose, D-sorbose, L-sorbose, D-tagatose and L-tagatose.

In a further preferred embodiment, the radicals $R^{(I)}$ $R^{(II)}$ and $R^{(III)}$ independently of each other are selected from the group which consists of hydrogen or alkyl groups of the general formula $-(CH_2)_n-CH_3$, wherein n is an integer from 0 to 19, preferably from 1 to 17.

In a further preferred embodiment, the radicals $R^{(I)}$ $R^{(II)}$ and $R^{(III)}$ independently of each other are selected from the group which consists of hydrogen, methyl, ethyl, prop-1-yl, prop-2-yl, but-1-yl, but-2-yl, 2-methylprop-yl, 2-methylprop-2-yl, pent-1-yl, pent-2-yl, pent-3-yl, 2-methylbut-1-yl, 2-methylbut-2-yl, 2-methylbut-3-yl, 2-methylbut-4-yl, 2,2-dimethylprop-1-yl, hex-1-yl, hex-2-yl, hex-3-yl, hept-1-yl, oct-1-yl, 2-methylpent-1-yl, 2-methylpent-2-yl, 2-methylpent-3-yl, 2-methylpent-4-yl, 2-methylpent-5-yl, 3-methylpent-1-yl, 3-methylpent-2-yl, 3-methylpent-3-yl, 2,2-dimethylbut-1-yl, 2,2-dimethylbut-3-yl, 2,2-dimethylbut-4-yl, 2,3-dimethylbut-1-yl and 2,3-dimethylbut-2-yl. In a particularly preferred embodiment, the radicals $R^{(I)}$ $R^{(II)}$ and $R^{(III)}$ independently of each other are selected from the group which consists of methyl, ethyl, prop-1-yl, but-1-yl, pent-1-yl, hex-1-yl, hept-1- and oct-1-yl.

In a further preferred embodiment, the radicals $R^{(I)}$ $R^{(II)}$ and $R^{(III)}$ independently of each other are selected from the group which consists of hydrogen or the radicals of Formulae (6) to (9):

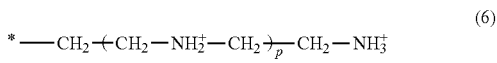
(6)

(7)

(8)

(9)

wherein p means an integer from 1 to 10, preferably from 1 to 7, further preferably from 1 to 3, and wherein s, r, q in each case independently of each other means an integer from 1 to 20, preferably from 1 to 8, further preferably from 1 to 4.

In a further preferred embodiment, the radical with Formula (5):

(5)

means a substituted or unsubstituted heterocyclic radical with 5 to 7 ring atoms which comprise at least 1 carbon atom and 1 to 4 nitrogen atoms as well as optionally 1 or 2 oxygen or sulfur atoms, wherein the heterocyclic radical is saturated or unsaturated.

By the term "heterocyclic" are meant according to the invention cyclic compounds with ring-forming atoms from at least two different chemical elements, preferably carbon, nitrogen, oxygen or sulfur.

In a further preferred embodiment, the heterocyclic radical with 5 to 7 ring atoms is selected from the group which consists of azolylene, azolinylene, azolidinylene, diazolylene, diazolinylene, diazolidinylene, triazolylene, triazolinylene, triazolidinylene, tetrazolylene, thiazolylene, thiadiazolylene, oxazolylene, oxazolinylene, oxazolidinylene, oxadiazolylene, azinylene, dihydroazinylene, tetrahydroazinylene, diazinylene, dihydrodiazinylene, tetrahydrodiazinylene, tetrahydrodiazinylene, triazinylene, tetrazinylene, oxazinylene, dihydrooxazinylene, tetrahydrooxazinylene, thiazinylene, azepanylene, azepinylene, diazepinylene or thiaazepinylene, wherein the above-named heterocyclic radicals are unsubstituted or can be substituted with at least one radical which is selected from the group which consists of phenyl, benzyl, straight-chained or branched alkyl with 1 to 20 C atoms, amino, methylamino, and dimethylamino.

In a further preferred embodiment, the heterocyclic radical is formed from compounds with 5 to 7 ring atoms, wherein these compounds are selected from the group which consists of pyrrolidine, pyrrole, imidazole, imidazoline, imidazolidine, pyrazole, pyrazoline, pyrazolidine, triazole, tetrazole, oxazole, oxazoline, oxazolidine, isoxazole, isoxazoline, isoxazolidine, thiazole, thiazoline, thiazolidine, isothiazole, isothiazoline, isothiazolidine, oxadiazolene, thiadiazolene, piperidine, pyridine, piperazine, pyrazines, pyrimidine, pyridazine, oxazinene, dihydrooxazinene, tetrahydrooxazinene, preferably morpholine, thiazine, triazinene, azepinene, azepane, diazepinene and thiazepinene, wherein the above-named compounds are unsubstituted or can be substituted with at least one radical which is selected from the group which consists of phenyl, benzyl, straight-chained or branched alkyl with 1 to 20 C atoms, amino, methylamino, and dimethylamino.

In a particularly preferred embodiment, the heterocyclic radical with 5 to 7 ring atoms is selected from the group which consists of piperazinium-1-yl, 4-methylpiperazinium-1-yl, 4-morpholinium, pyrrolidinium-1-yl, pyridinium-1-yl and 4-aminopyridinium-1-yl.

In a further preferred embodiment, the radical with Formula (5):

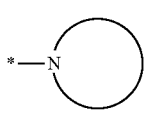

(5)

means a substituted or unsubstituted heteroaryl radical with 5 to 7 ring atoms which comprise at least 1 carbon atom and 1 to 4 nitrogen atoms as well as optionally 1 or 2 oxygen or sulfur atoms, or a substituted or an unsubstituted cyclic heteroalkyl radical with 5 to 7 ring atoms which comprise at least 1 carbon atom and 1 to 4 nitrogen atoms as well as optionally 1 or 2 oxygen or sulfur atoms, or a substituted or unsubstituted cyclic heteroalkenyl radical with 5 to 7 ring atoms which comprise at least 1 carbon atom and 1 to 4 nitrogen atoms as well as optionally 1 or 2 oxygen or sulfur atoms [represents].

In a further preferred embodiment, the radical with Formula (5):

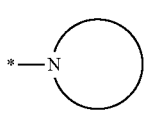

(5)

means a substituted or unsubstituted heterocyclic radical with 5 to 7 ring atoms which is selected from the group which consists of the radicals of Formulae (60) to (84c):

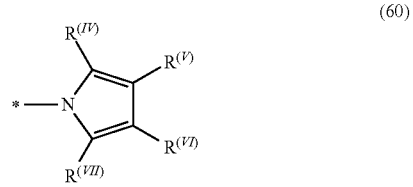

(60)

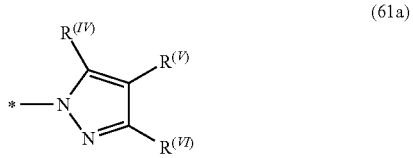

(61a)

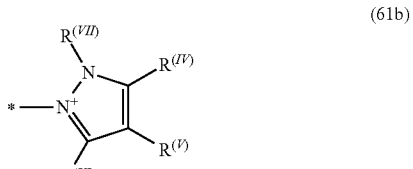

(61b)

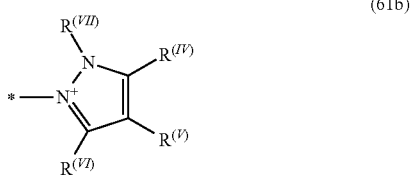

(62a)

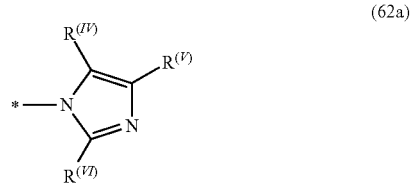

(62b)

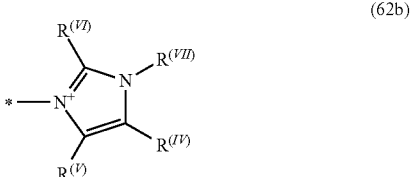

(63a)

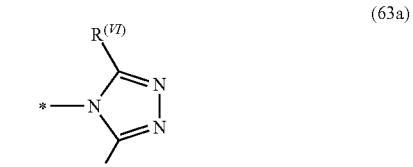

(63b)

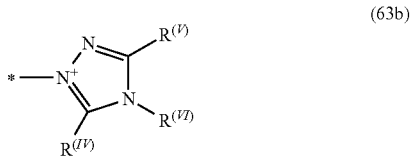

(64a)

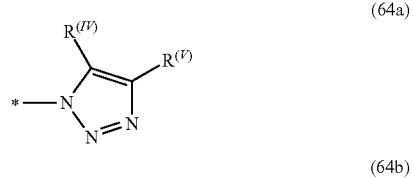

(64b)

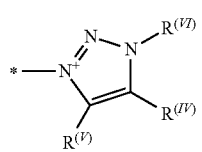
(64c)
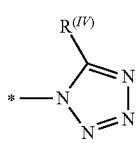
(65a)
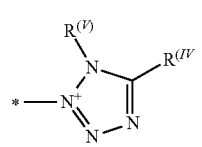
(65b)
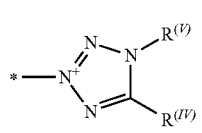
(65c)
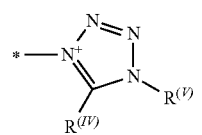
(65d)
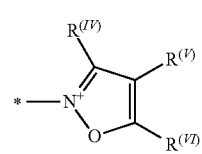
(66)
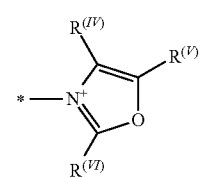
(67)
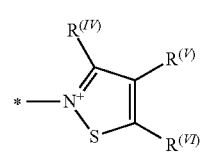
(68)
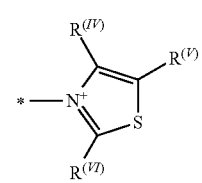
(69)
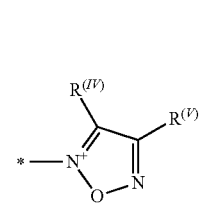
(70)
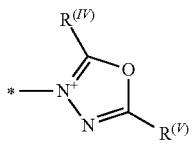
(71)
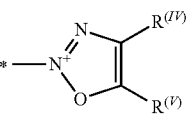
(72a)
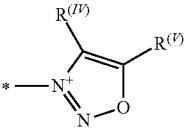
(72b)
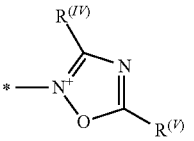
(73a)
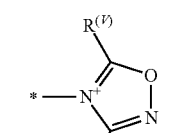
(73b)
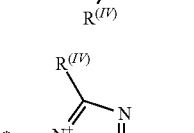
(74a)
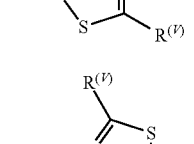
(74b)
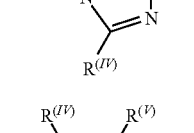
(75)
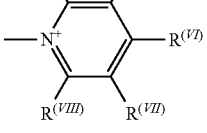
(76)
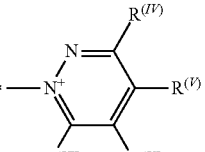
(77)
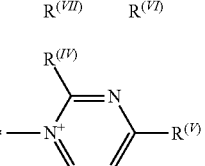

(78) 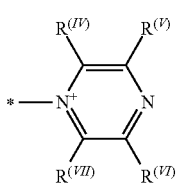

(79) 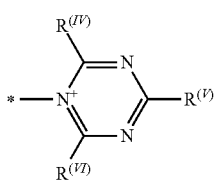

(80a) 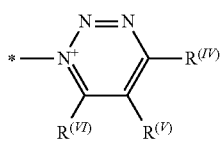

(80b) 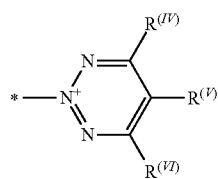

(81a) 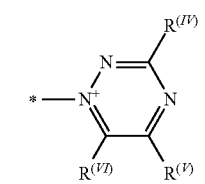

(81b) 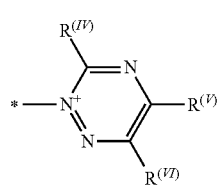

(81c) 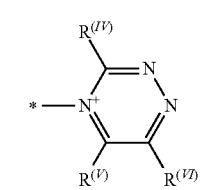

(82) 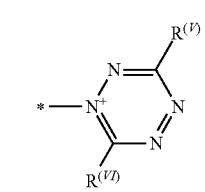

(83a) 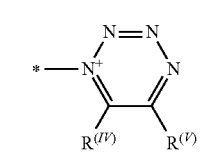

(83b) 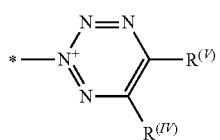

(84a) 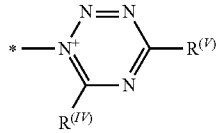

(84b) 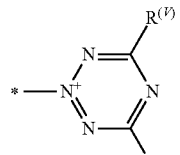

(84c) 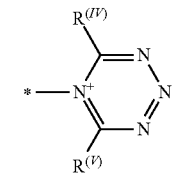

and wherein each of the radicals $R^{(IV)}$, $R^{(V)}$, $R^{(VI)}$, $R^{(VII)}$ and $R^{(VIII)}$ independently of each other in each case is selected from the group which consists of hydrogen, phenyl, benzyl, C1 to C20 alkyl, which can be straight-chained or branched, amino, methylamino, and dimethylamino.

In a further preferred embodiment, the 1H-phenalene-1-one derivative has Formula (1), wherein R1 to R8, which can in each case be the same or independently of each other different, are in each case selected from the group which consists of hydrogen and the radical —$(CH_2)_k$—X, with the proviso that at least one radical R1 to R8, preferably R1, is not hydrogen and wherein k is an integer from 1 to 20, preferably 1 to 6, further preferably 1 to 4, further preferably is 1, and wherein X is a radical with Formula (5):

(5) 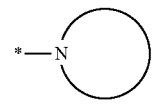

which means a substituted or unsubstituted heterocyclic radical with 5 to 7 ring atoms which is selected from the group which consists of the radicals of Formulae (60) to (84c).

In a further preferred embodiment of the compound with Formula (1), R2 to R8 are hydrogen and R1 is —$(CH_2)_k$—X, wherein k is an integer from 1 to 20, preferably from 1 to 19, preferably from 1 to 17, further preferably from 1 to 13, further preferably from 1 to 9, further preferably from 1 to 6, further preferably from 1 to 4, further preferably is 1, and wherein X is a radical with Formula (5):

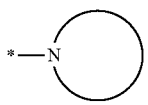
(5)

which means a substituted or unsubstituted heterocyclic radical with 5 to 7 ring atoms which is selected from the group which consists of the radicals of Formulae (60) to (84c).

In a further preferred embodiment, the 1H-phenalene-1-one derivative has Formula (1), wherein R1 to R8, which can in each case be the same or independently of each other different, are in each case selected from the group which consists of hydrogen and the radical —(CH$_2$)$_k$—X, with the proviso that at least one radical R1 to R8, preferably R1, is not hydrogen and wherein k is an integer from 1 to 20, preferably 1 to 6, further preferably 1 to 4, further preferably is 1, and wherein X is selected from the group which consists of the radicals of Formulae (10) to (33):

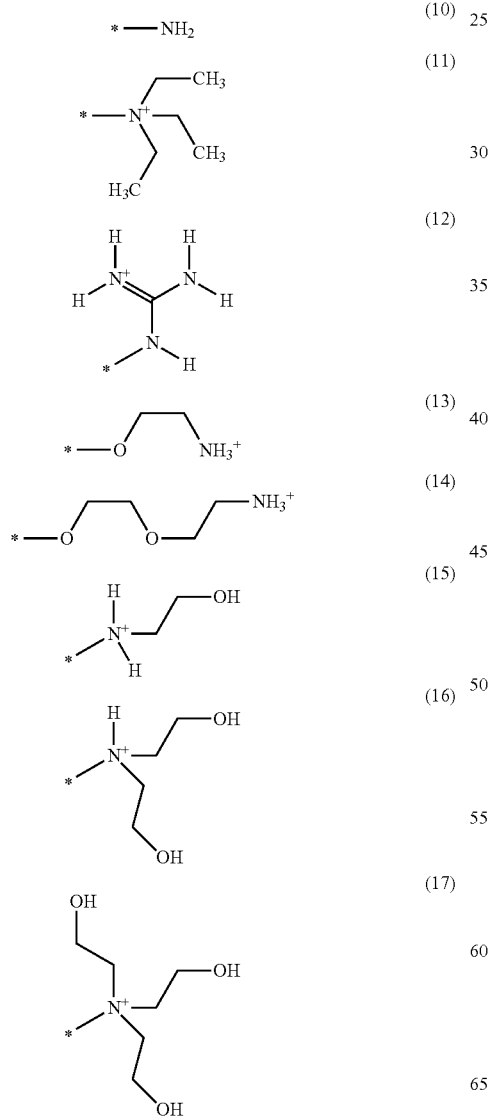

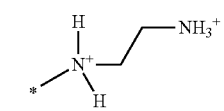
(18)

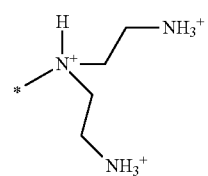
(19)

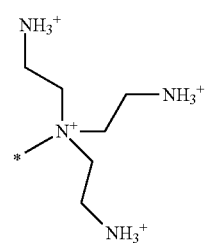
(20)

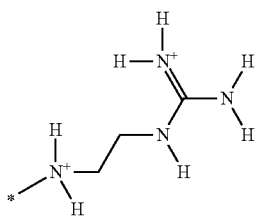
(21)

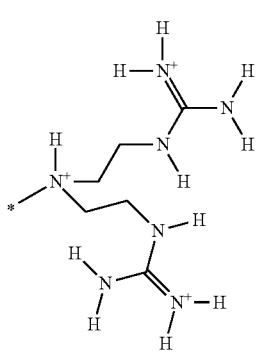
(22)

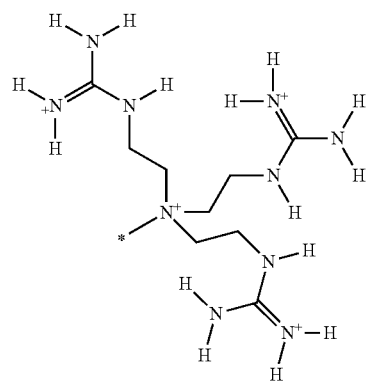
(23)

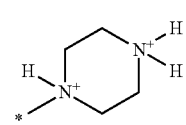
(24)

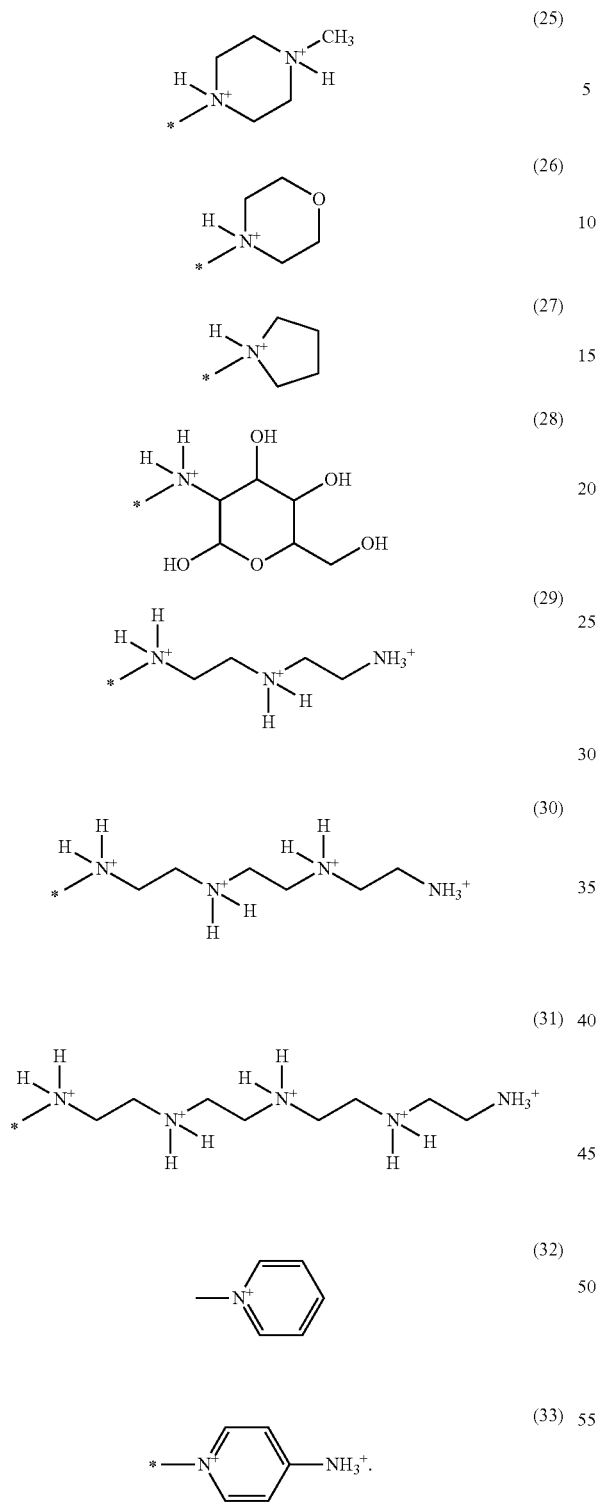
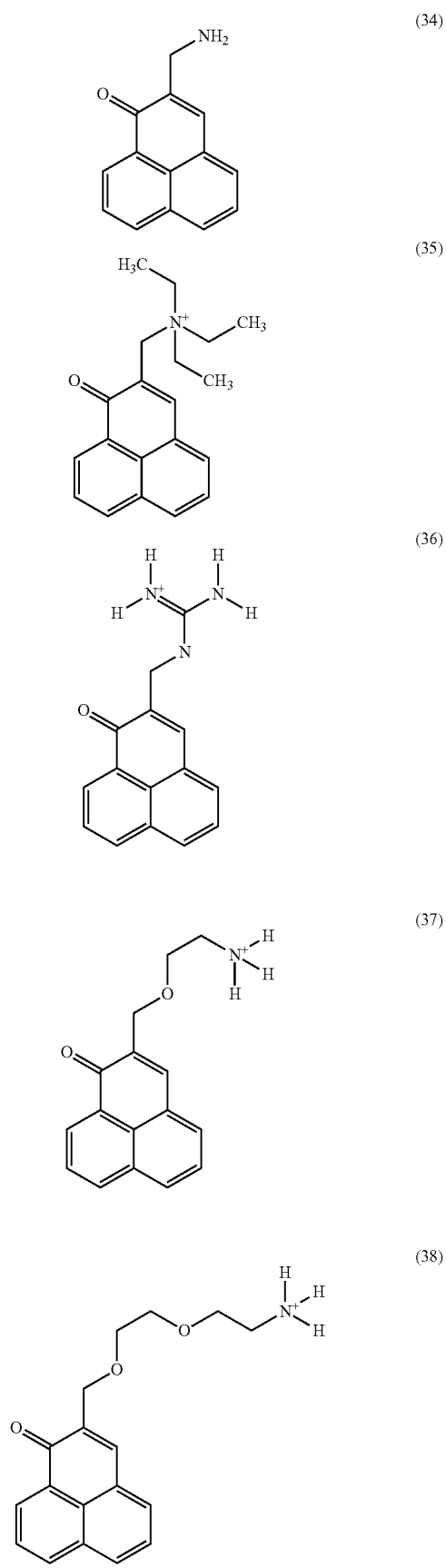
In a further preferred embodiment, R2 to R8 are hydrogen and R1 is —(CH$_2$)$_k$—X, wherein X is selected from the group which consists of the radicals of Formulae (9) to (33). In this preferred embodiment, the 1H-phenalene-1-one derivative according to the invention is therefore selected from the group which consists of the compounds with Formulae (34) to (57):

(39) 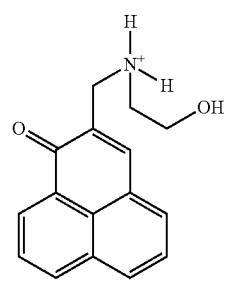
(40) 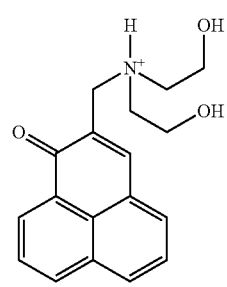
(41) 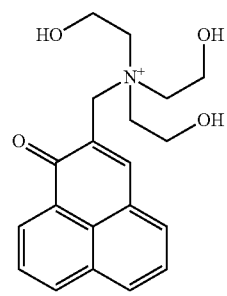
(42) 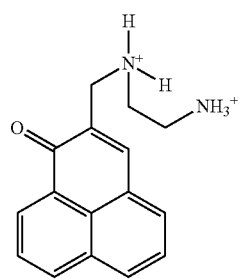
(43) 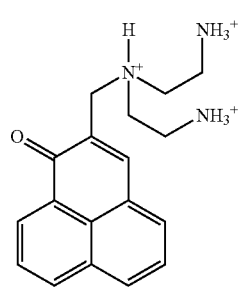
(44) 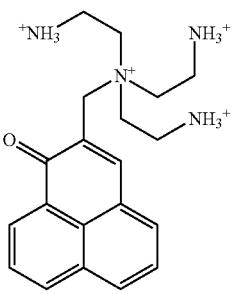
(45) 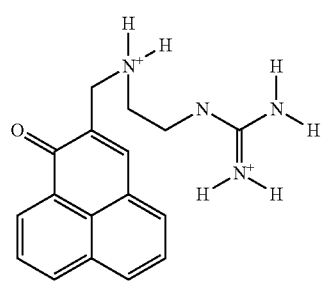
(46) 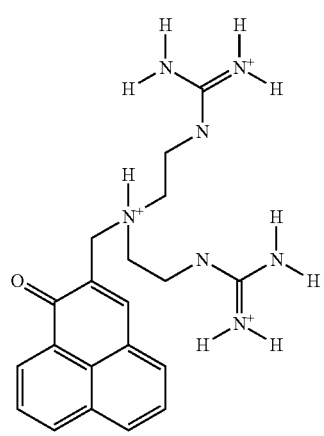
(47) 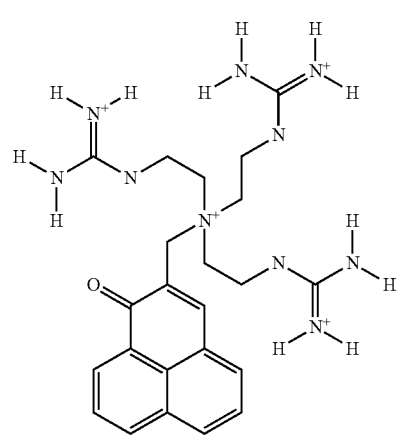

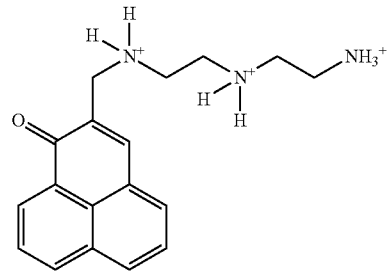
(48)
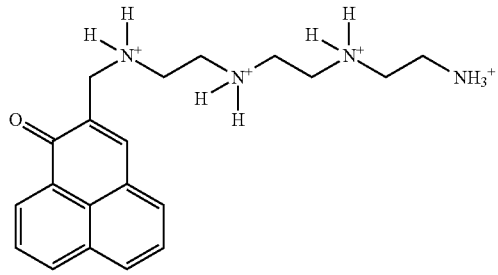
(49)
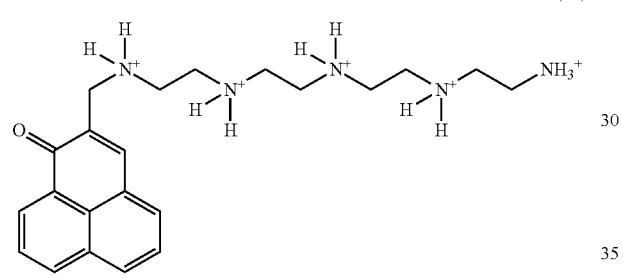
(50)
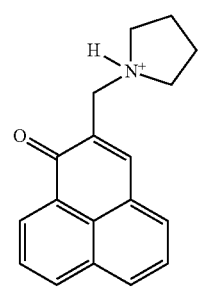
(51)
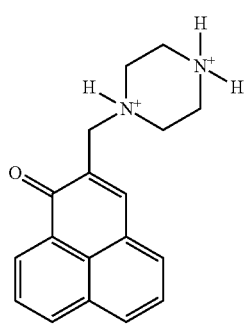
(52)
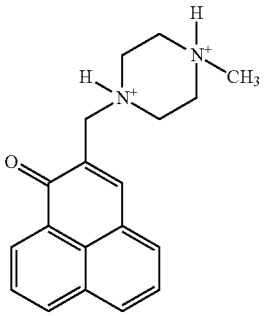
(53)
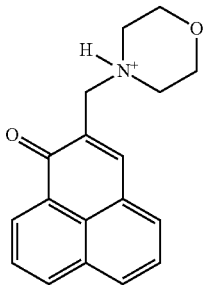
(54)
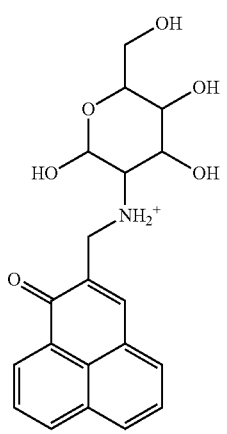
(55)
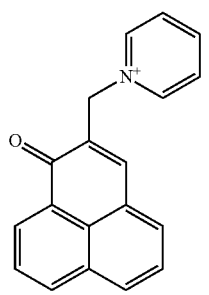
(56)

-continued

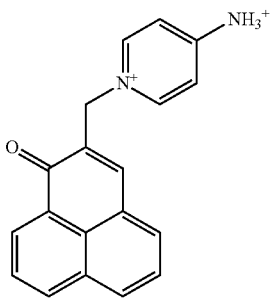
(57)

In a further preferred embodiment, the 1H-phenalene-1-one derivative has Formula (1), wherein R1 to R8, which can in each case be the same or independently of each other different, are in each case selected from the group which consists of hydrogen and the radical —$(CH_2)_k$—X, wherein k is an integer from 1 to 6, preferably from 1 to 5, further preferably from 1 to 4, further preferably is 1, wherein X is an organic radical which contains a) at least one neutral, protonatable nitrogen atom and/or b) at least one positively charged nitrogen atom, with the proviso that at least one radical R1 to R8, preferably R1, is not hydrogen and the molecular weight of the 1H-phenalene-1-one derivative of Formula (1) is less than 1000 g/mol, preferably less than 890 g/mol, further preferably less than 750 g/mol, further preferably less than 660 g/mol, still further preferably less than 600 g/mol, still further preferably less than 570 g/mol.

The method according to the invention for producing a 1H-phenalene-1-one derivative of Formula (1) comprises the following steps:
(A1) reacting 1H-phenalene-1-one with at least one alkylating agent of the formula Y—$(CH_2)_h$—Z, wherein Y is selected from the group which consists of H, Cl, Br, I, p-toluene sulfonyl (OTs), which is also called tosyl, methanesulfonyl (OMs), which is also called mesyl, OH and alkyl$_2$S$^+$, preferably H, Cl, Br and I, wherein alkyl can be the same or independently of each other different and preferably means methyl, ethyl, propyl or butyl, optionally in the presence of a catalyst, preferably Lewis acid or Brønsted acid, obtaining a compound with Formula (58):

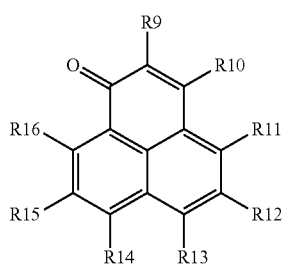
(58)

wherein R9 to R16, which can be the same or independently of each other different, mean in each case hydrogen or the radical —$(CH_2)_h$—Z, wherein h means an integer from 0 to 20, preferably from 1 to 19, preferably from 1 to 17, further preferably from 1 to 13, further preferably from 1 to 9, further preferably from 1 to 6, further preferably from 1 to 4, preferably means 1, and wherein Z is selected from the group which consists of Cl, Br, I, OTs, OMs, OH and alkyl$_2$S$^+$, wherein alkyl can be the same or independently of each other different and preferably means methyl, ethyl, propyl or butyl, with the proviso that at least 1 radical R9 to R16, preferably R9, is not hydrogen, or
(A2) reacting 1H-phenalene-1-one with formaldehyde and at least one halogen hydracid, optionally in the presence of a catalyst, obtaining a compound with Formula (58):

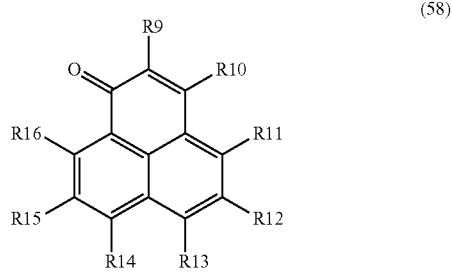
(58)

wherein R9 to R16, which can be the same or independently of each other different, mean in each case hydrogen or the radical —$CH_2$—W, and wherein W is selected from the group which consists of Cl, Br and I, with the proviso that at least 1 radical $R^9$ to $R^{16}$ is not hydrogen,
(B) reacting the compound obtained in step (A1) or (A2) with Formula (58) with an organic compound which contains a) at least one neutral, protonatable nitrogen atom and/or b) at least one positively charged nitrogen atom, optionally in the presence of a base, and optionally
(C) removing any amino protecting groups present, obtaining the 1H-phenalene-1-one derivative according to the invention of Formula (1).

The halogen hydracid used in step (A2) is preferably HCl, HBr, HI or mixtures thereof. HCl has proved to be a very suitable halogen hydracid. Preferably, in step (A2), the radical —$CH_2$—W is —$CH_2$—Cl.

In a further preferred embodiment of the method according to the invention, in step (A1) a compound of Formula (58) is obtained:

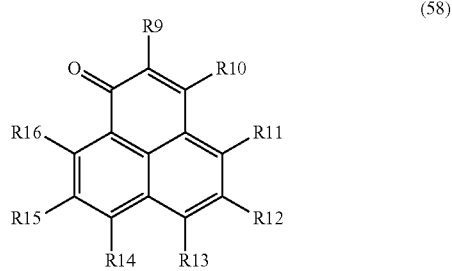
(58)

wherein $R^9$ means the radical —$(CH_2)_h$—Z, wherein h means an integer from 1 to 20, preferably from 1 to 19, preferably from 1 to 17, further preferably from 1 to 13, further preferably from 1 to 9, further preferably from 1 to 6, further preferably from 1 to 4, preferably means 1, and wherein Z is selected from the group which consists of Cl, Br, I, OTs, OMs, OH and alkyl$_2$S$^+$, wherein alkyl can be the same or independently of each other different and preferably means methyl, ethyl, propyl or butyl, and R10 to R16 mean hydrogen.

In a further preferred embodiment of the invention, in step (A2) a [compound] of Formula (58) is obtained, wherein R9 means the radical —$CH_2$—W, wherein W is selected from the group which consists of Cl, Br and I. R9 preferably means the radical —$CH_2$—Cl.

The alkylation of 1H-phenalene-1-one can take place for example by means of Friedel-Crafts alkylation which makes the alkylation of aromatics possible.

In a preferred embodiment, the method comprises the following steps:

(A1) reacting 1H-phenalene-1-one with at least one haloalkylating agent, optionally in the presence of a catalyst, preferably Lewis-acid or Brønsted-acid, obtaining a compound of Formula (58):

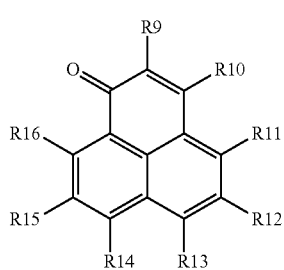

(58)

wherein R9 to R16, which can be the same or independently of each other different, are in each case selected from the group which consists of hydrogen and the radical —$(CH_2)_i$-Hal, wherein i means an integer from 1 to 20, preferably from 1 to 19, preferably from 1 to 17, further preferably from 1 to 13, further preferably from 1 to 9, further preferably from 1 to 6, further preferably from 1 to 4, and wherein Hal means a halogen atom which is selected from the group which consists of Cl, Br and I, with the proviso that at least 1 radical R9 to R16, preferably R9, is not hydrogen, or (A2) reacting 1H-phenalene-1-one with formaldehyde and at least one halogen hydracid, optionally in the presence of a catalyst, obtaining a compound with Formula (58):

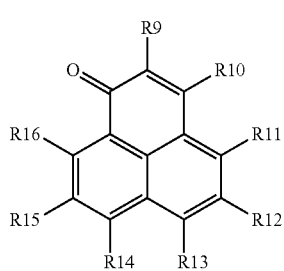

(58)

wherein R9 to R16, which can be the same or independently of each other different, mean in each case hydrogen or the radical —$CH_2$—W, and wherein W is selected from the group which consists of Cl, Br and I, with the proviso that at least 1 radical $R^9$ to R16 is not hydrogen.

(B) reacting the compound obtained in step (A1) or (A2) with Formula (58) with an organic compound which contains a) at least one neutral, protonatable nitrogen atom and/or b) at least one positively charged nitrogen atom, optionally in the presence of a base, and optionally (C) removing any amino protecting groups present, obtaining the 1H-phenalene-1-one derivative according to the invention of Formula (1).

The halogen hydracid used in step (A2) is preferably HCl, HBr, HI or mixtures thereof. HCl has proved to be a very suitable halogen hydracid. Preferably, in step (A2), the radical —$CH_2$—W is —$CH_2$—Cl.

A suitable alkylating agent is known from the state of the art and carries the radical —$(CH_2)_h$—Z, wherein h means an integer from 1 to 20, preferably from 1 to 19, preferably from 1 to 17, further preferably from 1 to 13, further preferably from 1 to 9, further preferably from 1 to 6, further preferably from 1 to 4, preferably means 1, and wherein Z is selected from the group which consists of Cl, Br, I, OTs, OMs, OH and alkyl$_2$S$^+$, wherein alkyl preferably means the same or independently of each other methyl, ethyl, propyl or butyl.

A suitable haloalkylating agent is known from the state of the art and is selected from the group which consists of aldehydes and hydrogen halide, haloalkyl ethers, haloalkyl sulfides, acetalene and hydrogen halide, di- and polyhaloalkanes, haloalkenes, haloalcohols, haloalkyl sulfates, haloalkyl p-tosylates, haloalkyl mesylates and haloalkyl esters of inorganic acids, wherein a suitable haloalkylating agent transmits the radical —$(CH_2)_i$-Hal, wherein i means an integer from 1 to 20, preferably from 1 to 19, preferably from 1 to 17, further preferably from 1 to 13, further preferably from 1 to 9, further preferably from 1 to 6, further preferably from 1 to 4, preferably means 1, and wherein Hal means a halogen atom, preferably Cl, Br or I.

The haloalkylating agent is preferably selected from the group which consists of aldehydes of the general formula H—$(CH_2)_{(i-1)}$—CHO or acetals thereof and hydrogen halide, haloalkyl ethers of the general formula Hal-$(CH_2)_i$—O—$R^{17}$, haloalkanes of the general formula Hal-$(CH_2)_i$—F, haloalcohols of the general formula Hal-$(CH_2)_i$—OH, haloalkyl sulfates of the general formula Hal-$(CH_2)_i$—OSO$_3$H, haloalkyl mesylates of the general formula Hal-$(CH_2)_i$—OMs, and haloalkyl p-tosylates of the general formula Hal-$(CH_2)_i$—OTs, wherein i means an integer from 1 to 20, preferably from 1 to 19, preferably from 1 to 17, further preferably from 1 to 13, further preferably from 1 to 9, further preferably from 1 to 6, further preferably from 1 to 4, preferably means 1, and wherein Hal means a halogen atom which is selected from the group which consists of Cl, Br and I, and wherein $R^{17}$ means an alkyl radical with 1 to 20 C atoms.

In a preferred embodiment, the haloalkylation of 1H-phenalene-1-one in step (B) of the method according to the invention takes place in the presence of at least one catalyst, preferably Lewis acid and/or Brønsted acid.

Suitable catalysts are known from the state of the art. Lewis acids suitable as catalyst are for example AlCl$_3$, FeCl$_3$, FeBr$_3$, ZnCl$_2$, SnCl$_4$, BF$_3$ or TiCl$_4$. Brønsted acids suitable as catalyst are for example H$_2$SO$_4$, H$_3$PO$_4$, H$_2$SnCl$_6$×6H$_2$O, HCOOH or CH$_3$COOH.

The compound obtained in step (B) with Formula (58) can then be reacted in step (C) with an organic compound which contains a) at least one neutral, protonatable nitrogen atom and/or b) at least one positively charged nitrogen atom, obtaining the 1H-phenalene-1-one derivative according to the invention of Formula (1), optionally in the presence of a base, for example NaOH, LiOH, KOH, Na$_2$CO$_3$, K$_2$CO$_3$ or Cs$_2$CO$_3$.

In a preferred embodiment, the organic compound which contains a) at least one neutral, protonatable nitrogen atom and/or b) at least one positively charged nitrogen atom is selected from the group which consists of the compounds of Formulae (2a), (2b) and (2c):

(2a)

-continued

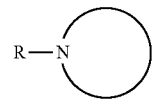
(2b)

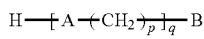
(2c)

wherein the radical R is selected from hydrogen, a protecting group PG or a free electron pair and wherein A is an oxygen or a sulfur atom or a nitrogen atom which can be neutral or positively charged and wherein p is an integer from 1 to 8 and q is an integer from 1 to 100, preferably from 1 to 10, and wherein B is selected from the group which consists of the radicals of Formulae (3), (4) and (5):

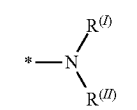
(3)

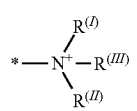
(4)

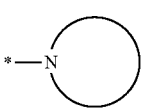
(5)

and wherein each of the radicals $R^{(I)}$, $R^{(II)}$ and $R^{(III)}$ independently of each other is selected from PG, monosaccharide, preferably pentose or hexose, or C1 to C20 alkyl, preferably C2 to C18 alkyl, which can be straight-chained or branched, preferably straight-chained, wherein the above-named alkyl radicals are unsubstituted or can be substituted with at least one radical which is selected from the group which consists of —NH(PG), —N(PG)$_2$, —N(PG)CH$_3$, dimethylamino, trimethylammonio, =N(PG), methylimino, protected amidino, hydroxy and protected guanidino, wherein the radical PG means an amino protecting group.

Suitable amino protecting groups PG are known from the state of the art and comprise for example the radicals 1-(1-adamantyl)-1-methylethoxycarbonyl (Adpoc), allyloxycarbonyl (Alloc), benzyloxycarbonyl (Cbz), di-tert-butyloxycarbonyl (Boc), 9-fluorenylmethoxycarbonyl (Fmoc), trifluoroacetyl (Tfa) or triphenylmethyl (Trt).

In a further preferred embodiment, the radical with Formula (2a):

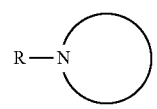
(2a)

means a substituted or unsubstituted heterocyclic radical with 5 to 7 ring atoms which comprise at least 1 carbon atom and 1 to 4 nitrogen atoms as well as optionally 1 or 2 oxygen or sulfur atoms, wherein the heterocyclic radical is saturated or unsaturated and wherein the radical R is selected from hydrogen, PG or a free electron pair.

In a further preferred embodiment, the substituted or unsubstituted heterocyclic radical with 5 to 7 ring atoms is selected from the heterocyclic radicals listed above.

In a further preferred embodiment, the radicals $R^{(I)}$ $R^{(II)}$ and $R^{(III)}$ independently of each other are selected from the group which consists of PG and the radicals of Formulae (6a), (7a), (8), (9a):

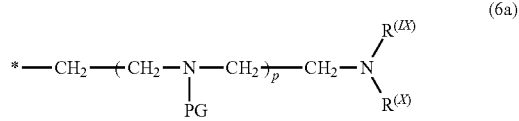
(6a)

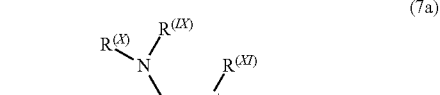
(7a)

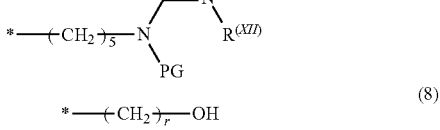
(8)

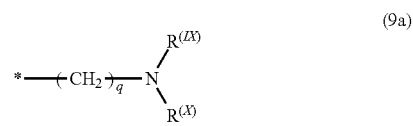
(9a)

wherein p means an integer from 1 to 10, preferably from 1 to 7, further preferably from 1 to 3, and wherein s, r, q in each case independently of each other mean an integer from 1 to 20, preferably from 1 to 8, further preferably from 1 to 4, preferably mean 1, and wherein the radicals $R^{(XI)}$, $R^{(X)}$, $R^{(XI)}$ and $R^{(XII)}$ independently of each other mean PG or methyl or hydrogen atom and wherein PG means an amino protecting group.

In a further preferred embodiment, the organic compound which contains a) at least one neutral, protonatable nitrogen atom and/or b) at least one positively charged nitrogen atom is selected from the group which consists of compounds of Formulae (10a) to (33a):

(10a)

(11a)

(12a)

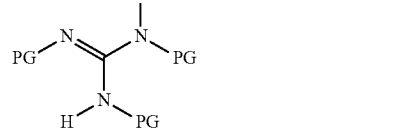
(12b)

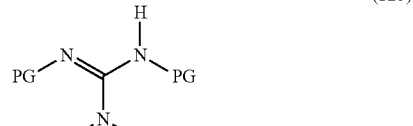

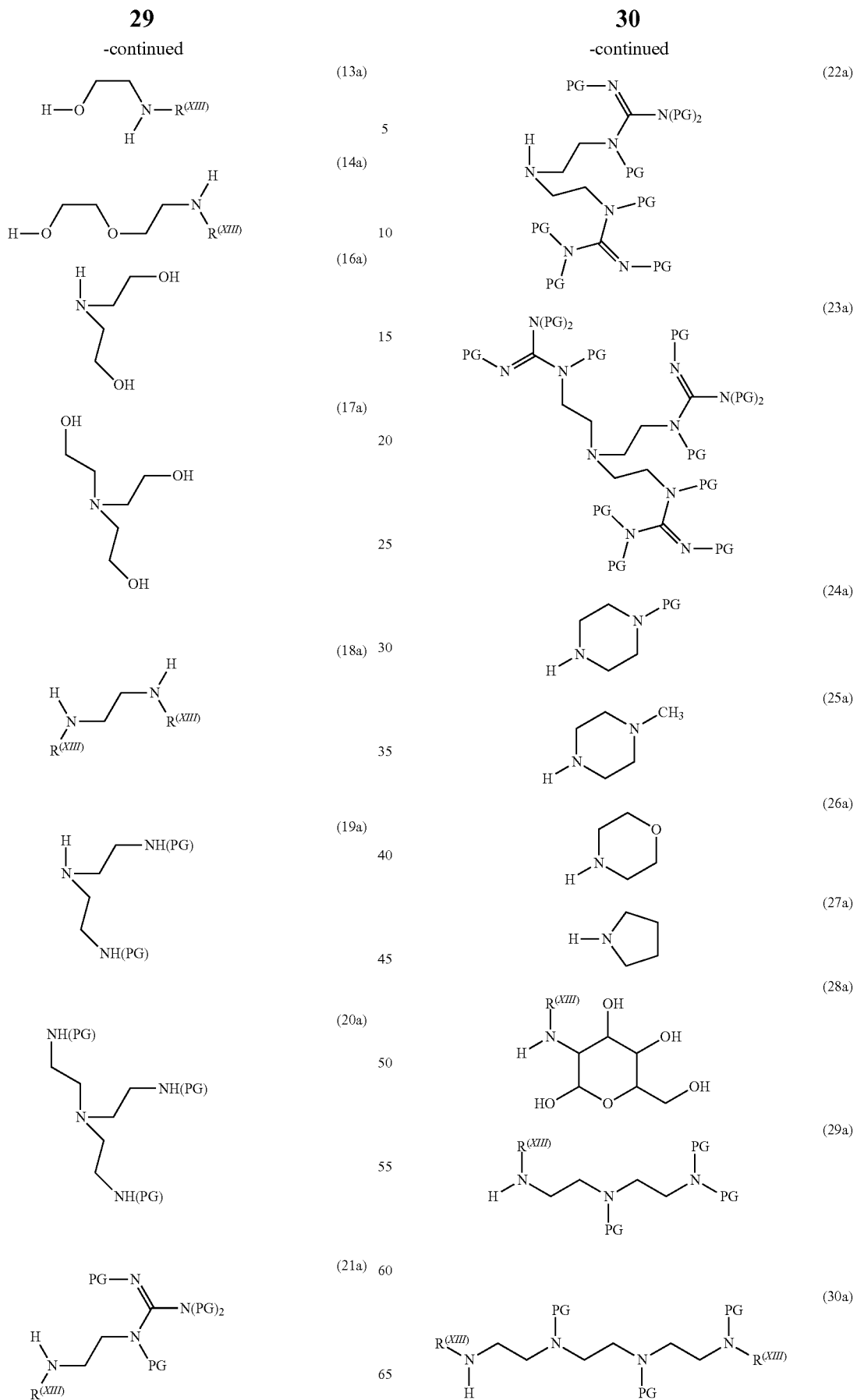

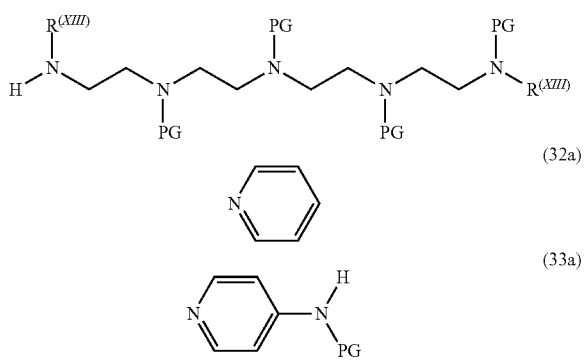

wherein the radical $R^{(XIII)}$ is PG or hydrogen and the radical PG means an amino protecting group, preferably benzyloxycarbonyl (Cbz) or di-tert-butyloxycarbonyl (Boc).

Suitable methods for removing the amino protecting group PG are known from the state of the art. For example, benzyloxycarbonyl (Cbz) can be removed again by catalytic hydrogenation accompanied by hydrogenolytic cleavage of the benzyl-heteroatom bond with subsequent decarboxylation of the thus-formed unstable carbamic acid or treatment with acids. Di-tert-butyloxycarbonyl (Boc) can be removed for example by acid hydrolysis. Allyloxycarbonyl (alloc) can be split off for example by the action of tetrakis(triphenylphosphane)palladium(0) and a nucleophile.

If different amino protecting groups PG are used in a synthesis, there is the possibility of the orthogonal protecting group strategy, wherein different amino functions of a molecule can be released one after the other in a targeted manner and made to react.

In a further preferred embodiment, steps (B) and/or (C) take place in the presence of one or more solvents. Step (B) can be carried out for example in the presence of dichloromethane (DCM), dimethylformamide (DMF) or acetonitrile (MeCN). Step (C) can be carried out for example in the presence of water/dichloromethane or toluene/tetrabutylammonium iodide (TBAI).

Single-celled or multi-celled microorganisms can be triggers of infectious diseases. By applying at least one pathogen-specific antagonist, for example an antibiotic, antimycotic or virostatic, the number of pathogenic agents can be reduced and/or the pathogenic agent can be inactivated. The application of a pathogen-specific antagonist can be systemic and/or topical.

In systemic application, the pathogen-specific antagonist is transmitted into the blood and/or lymphatic system of the body to be treated and thereby distributed throughout the whole body. If the pathogen-specific antagonist is taken systemically, a disintegration of the antagonist and/or side-effects can result, for example due to a biochemical conversion (metabolism) of the antagonist.

In topical application of the pathogen-specific antagonist, the antagonist is applied where it is to have a therapeutic effect, for example on an infected area of skin, while the healthy skin is not touched. Systemic side-effects can thus be largely avoided.

Superficial skin or soft tissue infections need not necessarily be treated with a systemic application of a pathogen-specific antagonist, because the antagonist can be applied directly to the infected areas of skin.

The pathogen-specific antagonists known until now have sometimes strong side-effects and interactions both in systemic and in topical application. In addition, in topical application, resistance can also develop as a result of an unreliable taking of medicines by the patient (compliance), in particular when antibiotics are used.

An alternative here is photodynamic inactivation of microorganisms, in which resistances to photodynamic inactivation are unknown. Irrespective of the type of microorganisms to be combatted and the associated infectious diseases, the number of pathogenic agents is reduced and/or the pathogenic agents are destroyed. For example, mixtures of different microorganisms, for example fungi and bacteria or different bacterial strains, can be combatted.

In a preferred embodiment, at least one 1H-phenalene-1-one derivative according to the invention or a pharmacologically compatible salt and/or ester and/or complex thereof is used as photosensitizer in the photodynamic inactivation of microorganisms, preferably in photodynamic therapy.

The 1H-phenalene-1-one derivative according to the invention has a high yield of singlet oxygen after irradiation with electromagnetic radiation of a suitable wavelength and energy density.

The electromagnetic radiation preferably lies in the visible spectral range, ultraviolet and/or infrared range. The electromagnetic radiation further preferably has a wavelength from a range of from 280 to 1000 nm, further preferably from 380 to 1000 nm.

The electromagnetic radiation further preferably has an energy density from a range of from 1 $\mu W/cm^2$ to 1 $MW/cm^2$, further preferably from 1 $mW/cm^2$ to 1 $kW/cm^2$.

The irradiation time can be varied depending on the type of microorganisms and/or the severity of the infection. The irradiation time preferably lies in a range of from 1 $\mu s$ to 1 h, further preferably from 1 ms to 1000 s.

The electromagnetic radiation is preferably generated by a radiation source which is selected from the group which consists of sun and artificial radiation sources, for example UV lamp, IR lamp, fluorescent lamps, light-emitting diodes, laser or chemical light.

In addition, the inventors have surprisingly found that the 1H-phenalene-1-one derivative according to the invention or pharmacologically compatible salts and/or esters thereof preferably have a high affinity to microorganisms.

Because of the affinity, the 1H-phenalene-1-one derivative according to the invention can effectively bind to microorganisms and produce locally sufficient singlet oxygen in order to inactivate, preferably kill off, the microorganisms.

In this preferred use as photosensitizer, at least one 1H-phenalene-1-one derivative according to the invention is bound by microorganisms. After irradiation with electromagnetic radiation of a suitable wavelength and energy density, the microorganisms are inactivated, preferably killed off, by the reactive oxygen species (ROS) formed, preferably oxygen radicals and/or singlet oxygen.

The binding of at least one 1H-phenalene-1-one derivative according to the invention to microorganisms preferably also allows a staining or localization of microorganisms. The progress of the inactivation of microorganisms or the decolonization can thereby preferably also be followed.

According to the invention, by the term "decolonization" is meant the removal, preferably complete removal, of microorganisms.

In a further preferred embodiment, the 1H-phenalene-1-one derivative according to the invention or a pharmacologically compatible salt and/or ester and/or complex thereof is used in the inactivation of single-celled or multi-celled microorganisms which are preferably selected from the group which consists of viruses, archaea, bacteria, bacterial spores, fungi, for example mycelium fungi and yeasts, fungal spores, protozoa, algae and blood-transmissible parasites.

Body surfaces, for example skin or mucous membrane, of humans and animals, preferably mammals, can preferably be treated. In this preferred embodiment, at least one 1H-phenalene-1-one derivative according to the invention or a pharmacologically compatible salt and/or ester and/or complex thereof, preferably in a pharmaceutical preparation, is used in the disinfection and/or decolonization of skin or soft tissue surfaces, wherein preferably skin integrity is maintained.

In a further preferred embodiment, at least one 1H-phenalene-1-one derivative according to the invention or a pharmacologically compatible salt and/or ester and/or complex thereof is present in a pharmaceutical preparation for topical, preferably nasal, oral, anal, vaginal or dermal, application.

By topical application is also meant application on or in the ear, preferably the outer ear. The outer ear comprises the ear cartilage, the pinna, the earlobe and the outer auditory canal or also ear canal and the outside of the eardrum.

By topical application is likewise meant surface application in the nasal cavity, to mucous membranes, to the skin or any body cavity.

In a further preferred embodiment, at least one 1H-phenalene-1-one derivative according to the invention or a pharmacologically compatible salt and/or ester and/or complex thereof for producing a pharmaceutical preparation is used in the prophylaxis and/or treatment of an infectious, preferably viral, bacterial and/or mycotic, skin disease which is preferably selected from the group which consists of Staphylococcal scalded skin syndrome, impetigo, skin abscess, boil, carbuncle, phlegmon, cellulitis, acute lymphadenitis, pilonidal cyst, pyoderma, purulent dermatitis, septic dermatitis, suppurative dermatitis, erythrasma, erysipelas, acne vulgaris or fungal infection.

In a further preferred embodiment, at least one 1H-phenalene-1-one derivative according to the invention or a pharmacologically compatible salt and/or ester and/or complex thereof for producing a pharmaceutical preparation is used in wound healing, for example in post-operative healing disorders.

Preferably, at least one 1H-phenalene-1-one derivative according to the invention or a pharmacologically compatible salt and/or ester and/or complex thereof or a pharmaceutical preparation containing at least one 1H-phenalene-1-one derivative according to the invention or a pharmacologically compatible salt and/or ester and/or complex thereof is used in the disinfection and/or reduction of the bacterial count in infected wounds.

In a further preferred embodiment, at least one 1H-phenalene-1-one derivative according to the invention or a pharmacologically compatible salt and/or ester and/or complex thereof for producing a pharmaceutical preparation is used in the prophylaxis and/or treatment of infectious, preferably viral, bacterial and/or mycotic, diseases of the ear, of the upper airways, of the oral cavity, of the throat, of the larynx, of the lower airways and/or of the esophagus.

The predominance of pathogenic microorganisms is for example the main cause of infections in the oral cavity. The problem arises that the microorganisms are organized synergistically in biofilms with extremely complex structure. These biofilms, for example plaque or tooth deposit, consist of several layers with complex structure and contain proteins, carbohydrates, phosphates and microorganisms. Tooth deposit forms particularly where tooth surfaces cannot be kept free of deposits by natural or artificial cleaning. This circumstance makes it difficult to find access to the microorganisms incorporated in the biofilm.

Conventional therapies, such as for example antibiotics and rinsing solutions or mechanical tooth cleaning, can only be used to a limited extent, because either they do not directly influence the bacteria, for example can be metered out and applied only with difficulty in tooth cleaning, for example in antibiotics and rinsing solutions, or a general application is not justifiable because of negative side-effects.

In a preferred embodiment, at least one 1H-phenalene-1-one derivative according to the invention or a pharmacologically compatible salt and/or ester and/or complex thereof is used as photosensitizer in the photodynamic inactivation of microorganisms in the oral cavity.

In a further preferred embodiment, at least one 1H-phenalene-1-one derivative according to the invention or a pharmacologically compatible salt and/or ester and/or complex thereof for producing a pharmaceutical preparation is used in the treatment and/or prophylaxis of an infectious, preferably viral, bacterial and/or mycotic, disease of the dental tissue, preferably plaque, caries or pulpitis, and/or infectious, preferably viral, bacterial and/or mycotic, disease of the periodontium, preferably gingivitis, periodontitis, endodontitis or peri-implantitis.

In a further preferred embodiment, at least one 1H-phenalene-1-one derivative according to the invention or a pharmacologically compatible salt and/or ester and/or complex thereof or a pharmaceutical preparation containing at least one 1H-phenalene-1-one derivative according to the invention or a pharmacologically compatible salt and/or ester and/or complex thereof is used in the cleaning of teeth, dental prostheses and/or dental braces.

In a further preferred embodiment, the 1H-phenalene-1-one derivative according to the invention or a pharmacologically compatible salt and/or ester and/or complex thereof or a pharmaceutical preparation containing at least one 1H-phenalene-1-one derivative according to the invention or a pharmacologically compatible salt and/or ester and/or complex thereof is used in the nasal decolonization of microorganisms.

For example, methicillin-resistant *Staphylococcus aureus* (MRSA) strains persist for months in nasal colonization, as well as being highly resistant in the environment. A nasal decolonization, i.e. removal of the microorganisms, therefore normally also reduces the colonization in other parts of the body.

Furthermore, the present invention relates to a pharmaceutical composition containing at least one 1H-phenalene-1-one derivative according to the invention or a pharmacologically compatible salt and/or ester and/or complex thereof.

The pharmaceutical composition is preferably produced by mixing at least one compound of Formula (1) or a pharmacologically compatible salt and/or ester and/or complex thereof with one or more physiologically acceptable excipient(s) and/or support(s) and brought into a suitable dosage form.

A suitable dosage form of the pharmaceutical composition according to the invention is preferably selected from the group which consists of ointment, cream, gel, lotion, suspension, solution, for example in droplet or spray form, powder, microcapsule and paste.

The pharmaceutical composition according to the invention can be applied topically, preferably nasally, orally, anally, vaginally or dermally.

The pharmaceutically usual liquid or solid fillers and extenders, solvents, emulsifiers, lubricants, taste adjusters, colorings and/or buffer substances come into consideration as physiologically acceptable excipients.

In a further preferred embodiment, the pharmaceutical composition contains an effective quantity of at least one 1H-phenalene-1-one derivative according to the invention or a pharmacologically compatible salt and/or ester and/or complex thereof, wherein the effective quantity comprises from 0.01 µg to 1000 µg per gram of the composition, preferably from 0.1 µg to 500 µg per gram of the composition.

In a preferred embodiment of the invention, the pharmaceutical composition comprises at least one 1H-phenalene-1-one derivative according to the invention or a pharmacologically compatible salt and/or ester and/or complex thereof and at least one further pharmaceutically active constituent.

Preferably, the at least one further pharmaceutically active constituent is selected from the group which consists of antibiotics, antimycotics, virostatics, antihistamines, sympathomimetics, antihemorrhagics, emollients and skin-protection products, analgesics, disinfectants, immune sera and immunoglobulins, antiparasitic substances, insecticides, repellents and corticosteroids.

In a further preferred embodiment, at least one 1H-phenalene-1-one derivative according to the invention or a pharmacologically compatible salt and/or ester and/or complex thereof or a pharmaceutical preparation containing at least one 1H-phenalene-1-one derivative according to the invention or a pharmacologically compatible salt and/or ester and/or complex thereof is applied by the user himself and, optionally, subsequently irradiated with a suitable radiation source which generates electromagnetic radiation of a suitable wavelength and energy density.

In a further preferred embodiment, at least one 1H-phenalene-1-one derivative according to the invention or a pharmacologically compatible salt and/or ester and/or complex thereof or a preparation containing at least one 1H-phenalene-1-one derivative according to the invention or a pharmacologically compatible salt and/or ester and/or complex thereof is used in the inactivation of microorganisms in medical blood products.

In a preferred embodiment, at least one 1H-phenalene-1-one derivative according to the invention is used for the inactivation of microorganisms on surfaces of all types. Further preferably, the 1H-phenalene-1-one derivative according to the invention is used in surface cleaning and/or coating, preferably of medical devices, food packaging or sanitary products.

Further preferably, at least one 1H-phenalene-1-one derivative according to the invention is applied to and/or introduced into surfaces and, optionally, subsequently irradiated with a suitable radiation source which generates electromagnetic radiation of a suitable wavelength and energy density. Preferably, the at least one 1H-phenalene-1-one derivative according to the invention effects a "self-disinfection" of the surface during irradiation.

The irradiation can take place directly after the treatment of the surface with at least one 1H-phenalene-1-one derivative according to the invention, preferably after the application of the at least one 1H-phenalene-1-one derivative according to the invention to the surface and/or introduction of the at least one 1H-phenalene-1-one derivative according to the invention into the surface, and/or at a later point in time.

Further preferably, objects are treated which have a thermally-limited durability, for example objects made of thermoplastics, or which are corroded by disinfectants.

Objects which have a thermally-limited durability can be sterilized for example only insufficiently, because they lose their shape or become brittle at higher temperatures.

In addition, if the application of disinfectants is incorrect and/or excessive, resistance can develop as a result of selection of robust microorganisms, for example if the active ingredient concentration and exposure time and thus the germ-reducing action are inadequate.

In a further preferred embodiment, at least one 1H-phenalene-1-one derivative according to the invention is used for the inactivation of microorganisms on surfaces of medical devices, preferably invasive medical equipment such as for instance catheters, hollow probes, tubes or needles.

Preferably, the medical devices are selected from wound dressings, bandages, catheters, hollow probes, tubes or needles.

Further preferably, by medical devices are also meant dental casts or dental prostheses, for example dentures, crowns or implants.

Preferably, a treatment of the surface of medical devices with at least one 1H-phenalene-1-one derivative according to the invention and/or coating and/or immobilization of at least one 1H-phenalene-1-one derivative according to the invention on the surface of medical devices and subsequent irradiation with electromagnetic radiation of a suitable wavelength and energy density reduces, preferably prevents, the colonization of the treated surfaces by microorganisms.

The irradiation can take place directly after the treatment of the surface with at least one 1H-phenalene-1-one derivative according to the invention, preferably after the application of the at least one 1H-phenalene-1-one derivative according to the invention to the surface and/or introduction of the at least one 1H-phenalene-1-one derivative according to the invention into the surface, and/or at a later point in time, before or during the use of the treated medical device.

In a further preferred use of the at least one 1H-phenalene-1-one derivative according to the invention or a pharmacologically compatible salt and/or ester and/or complex thereof in wound dressings and/or bandages, for example cotton gauze, an irradiation with electromagnetic radiation of a suitable wavelength and energy density can take place during or after the application of a wound dressing and/or bandage which contains at least one 1H-phenalene-1-one derivative according to the invention or a pharmacologically compatible salt and/or ester and/or complex thereof, whereby a reduction, preferably inactivation, of microorganisms in the wound area or treated areas of skin subsequently result.

In a further preferred embodiment, the wound dressing and/or bandage comprises, in addition to at least one 1H-phenalene-1-one derivative according to the invention or a pharmacologically compatible salt and/or ester and/or complex thereof, further constituents, preferably absorbents, for example calcium alginate or polyurethane foam, or further pharmaceutically active substances.

In a further preferred embodiment, at least one 1H-phenalene-1-one derivative according to the invention is used for the inactivation of microorganisms on surfaces of food packaging.

In a further preferred embodiment, at least one 1H-phenalene-1-one derivative according to the invention is used for the inactivation of microorganisms in a liquid or liquid, preferably aqueous, preparation, for example dispersion paint.

Preferably, the liquid is water.

At least one 1H-phenalene-1-one derivative according to the invention can be used for the treatment of water for the drinks and food industry, the pharmaceutical, chemicals and cosmetics industry, the electrical industry. Furthermore, at least one 1H-phenalene-1-one derivative according to the invention can be used in drinking water and rain water treatment, the treatment of wastewater or in the treatment of water for use in air-conditioning technology.

In this preferred use of at least one 1H-phenalene-1-one derivative according to the invention, the liquid or liquid preparation can subsequently be irradiated with a suitable radiation source which generates electromagnetic radiation of a suitable wavelength and energy density. Preferably, the 1H-phenalene-1-one derivative according to the invention effects a "self-disinfection" of the liquid or of the liquid preparation during the irradiation.

In a further preferred use of the at least one 1H-phenalene-1-one derivative according to the invention, the 1H-phenalene-1-one derivative can be present bonded to a solid support and thus be used as part of a solid matrix. Particularly preferably, at least one 1H-phenalene-1-one derivative according to the invention bonded to a solid support is introduced into the liquid to be treated, preferably water or blood.

A polymer which carries at least one 1H-phenalene-1-one derivative according to the invention covalently bonded thereto is particularly preferred as support. This composition, comprising the support and at least one 1H-phenalene-1-one derivative according to the invention, develops an antimicrobial activity as soon as it is exposed to electromagnetic radiation of a suitable wavelength and energy density.

In addition, the present invention relates to a coated object which contains at least one 1H-phenalene-1-one derivative according to the invention and/or is coated therewith.

Preferably, the surface of the coated object has at least one 1H-phenalene-1-one derivative according to the invention.

The coated object can subsequently be irradiated with a suitable radiation source which generates electromagnetic radiation of a suitable wavelength and energy density. Preferably, the 1H-phenalene-1-one derivative according to the invention effects a "self-disinfection" of the surface of the coated object during the irradiation.

The irradiation can take place directly after the treatment of the coated object with at least one 1H-phenalene-1-one derivative according to the invention, preferably after the application of the at least one 1H-phenalene-1-one derivative according to the invention to the surface of the coated object and/or introduction of the at least one 1H-phenalene-1-one derivative according to the invention into the surface of the coated object, and/or at a later point in time, preferably before or during the use of the coated object.

Suitable objects are preferably selected from the group which consists of medical devices, food packaging or sanitary products.

A further preferred embodiment of the coated object involves particles coated with at least one 1-H-phenalene-one derivative according to the invention, for example inorganic or organic particles.

Further preferably, the particles comprise at least one 1H-phenalene-1-one derivative according to the invention which is present covalently bonded to the particles.

The invention is explained below using figures and examples, without being limited thereto.

EXAMPLE 1)-19)

Production of Different 1H-Phenalene-1-One Derivatives

Overview of the Syntheses

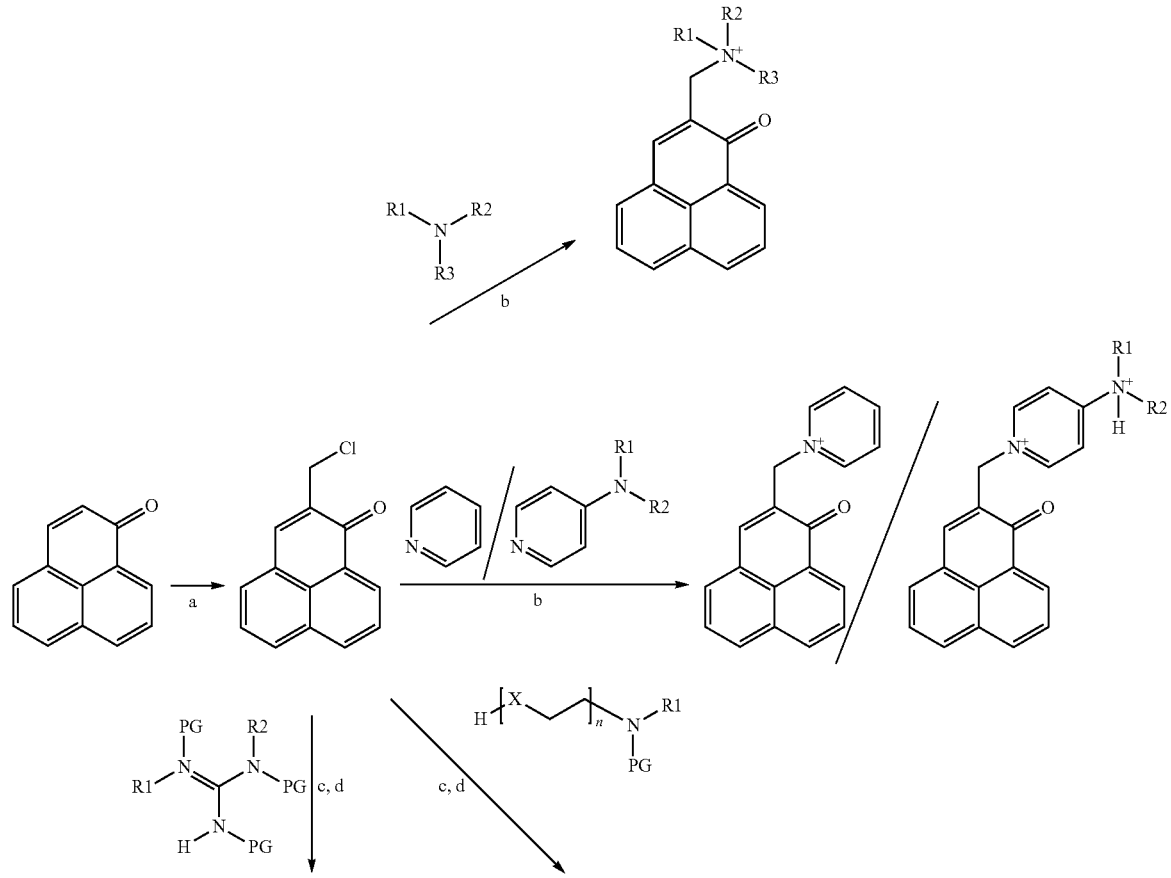

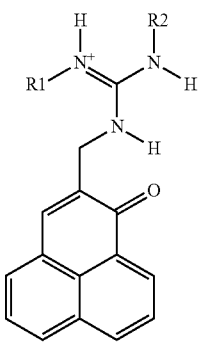
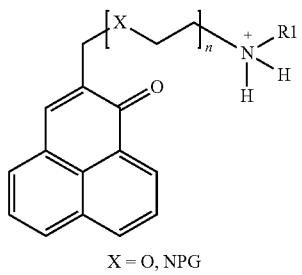
Conditions: a) HCHO, HOAc, H$_3$PO$_4$, HCl, 110° C.; b) DCM or DMF or MeCN, K$_2$CO$_3$ or Cs$_2$CO$_3$ or NaOH; c) NaOH, H$_2$O, DCM or toluene TBAI; d) PG=Boc: HCl, RT, 3h or PG=Cbz: Pd/C, H$_2$, 10 bar, RT, 1d, then HCl or PG=alloc: tetrakis(triphenylphosphane)Pd(0), Nu$^-$, 4h
NPG=nitrogen atom with protecting group (PG)
Specific Syntheses
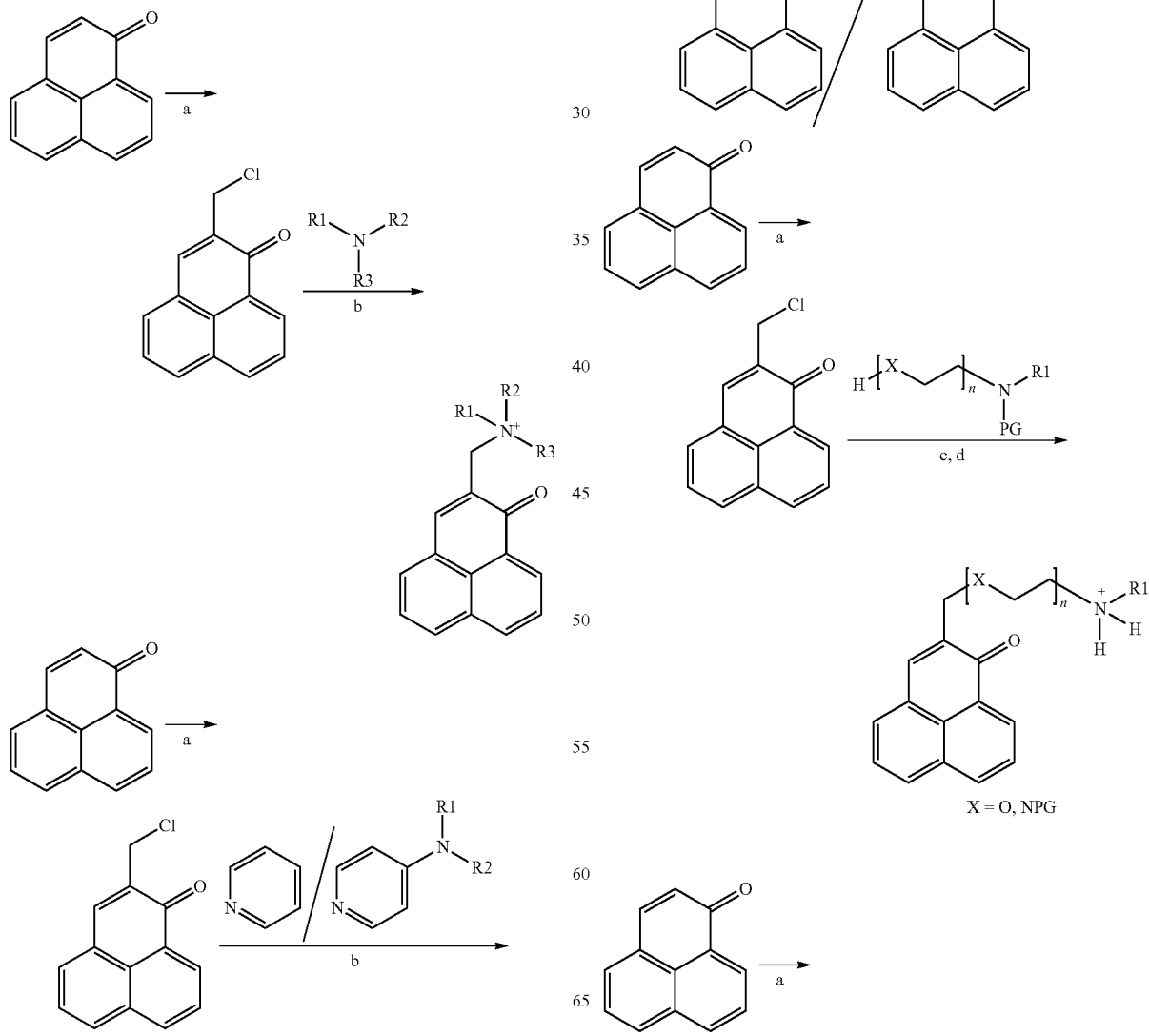

-continued

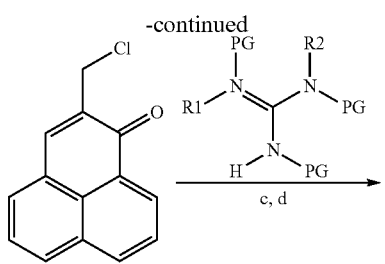

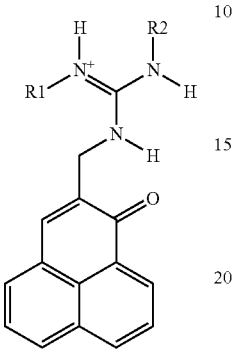

Conditions: a) HCHO, HOAc, H₃PO₄, HCl, 110° C.; b) DCM or DMF or MeCN, K₂CO₃ or CS₂CO₃ or NaOH; c) NaOH, H₂O, DCM or toluene, TBAI; d) PG=Boc: HCl, RT, 3h or PG=Cbz: Pd/C, H₂, 10 bar, RT, 1d, then HCl or PG=alloc: tetrakis(triphenylphosphane)Pd(0), Nu⁻, 4h Example 1

2-Chloromethyl-1H-phenalene-1-one

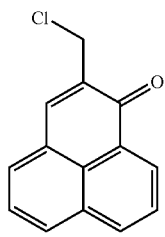 [SMILES: O=C1C(CCl)=Cc2cccc3cccc1c23]

Perinaphthenone (1.725 g, 9.58 mmol) and paraformaldehyde (5.49 g, 24 mmol) were heated in acetic acid (40 mL) and phosphoric acid (25 mL) at 110° C. accompanied by vigorous stirring until a clear solution formed. Aqueous HCl (32% w/w, 30 mL) was then added to the yellow solution slowly and in small quantities and heated under reflux for a further 8 h until a clear brown solution formed. After cooling to room temperature, 75 mL dist. water was added and the solution neutralized with K₂CO₃. The reaction mixture was extracted several times with CH₂Cl₂, the organic phases were combined, dried over MgSO₄ and the solvent drawn off. The oily product was purified by column chromatography (DCM/petrol ether (PE) 1:1, $R_f$=0.3). The product crystallizes out as a yellow powder (1.54 g, 6.72 mmol, 70% theoretical).

$^1$H-NMR (300 MHz, CDCl₃): δ [ppm]=4.68 (s, 2H), 7.60 (dd, 1H, J=7 Hz, 8 Hz), 7.78 (m, 2H), 7.92 (s, 1H), 8.03 (d, 1H, J=8 Hz), 8.20 (d, 1H, J=7.5 Hz), 8.64 (d, 1H, J=8 Hz); -$^{13}$C-NMR (75 MHz, CDCl₃): δ [ppm]=41.5 (1C), 126.8 (1C), 127.2 (1C), 127.2 (1C), 127.3 (1C), 129.0 (1C), 130.9 (1C), 132.0 (1C), 132.1 (1C), 132.2 (1C), 135.2 (1C), 135.6 (1C), 140.4 (1C), 183.5 (1C); —IR (neat): ν (cm⁻¹)=2940 (m), 2870 (m), 1630 (m), 1570 (m), 1206 (s), 1150 (s), 1050 (m), 775 (m), 636 (m); -MS (ESI-MS, CH₂Cl₂/MeOH+10 mmol NH₄OAc): e/z (%)=229.1 (100, MH⁺), 115.0 (16, (M+2H⁺)²⁺); -UV (MeOH): λ (ε)=249 (15400), 319 (2400), 360 (7300), 386 (6800);

Example 2

2-Aminomethyl-1H-phenalene-1-one

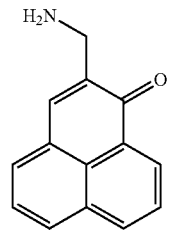 [SMILES: NCC1=Cc2cccc3cccc(c23)C1=O]

Potassium phthalimide (93 mg, 0.5 mmol) was placed in dry DMF (1 mL). A solution of 2-chloromethyl-1H-phenalene-1-one (114 mg, 0.5 mmol) in dry DMF (0.5 mL) was slowly added dropwise and the reaction mixture was then stirred overnight at room temperature. After addition of 5 mL DMF, the reaction mixture was heated for 12 h at 70° C., then ethanol (5 mL) and hydrazine (30 μL) were added and the batch was kept under reflux for another 2-3 h (DC control (EtOH/ethyl acetate (EE) 3:1). After cooling, the solvents were evaporated off and the residue was dissolved in a little warm ethanol. The solution was filtered off from the undissolved residue and evaporated to dryness. The crude product was purified by column chromatography (EE/EtOH 3:1, EE/EtOH 1:1, pure EtOH). 114 mg of a yellow, powdery solid (0.335 mmol, 67% theoretical) was obtained.

$^1$H-NMR (300 MHz, MeOD): δ [ppm]=4.70 (s, 2H), 7.80 (dd, 1H, J=7 Hz, 8 Hz), 7.88 (m, 2H), 7.97 (s, 1H), 8.06 (d, 1H, J=8 Hz), 8.22 (d, 1H, J=8 Hz), 8.60 (d, 1H, J=8 Hz); -IR (neat): ν (cm⁻¹)=2946 (m), 2880 (m), 1632 (m), 1580 (m), 1208 (m), 1152 (s), 1054 (m), 776 (m), 634 (m); -MS (ESI-MS, CH₂Cl₂/MeOH+10 mmol NH₄OAc): e/z (%)=210.1 (100, MH⁺), 105.6 (8, (M+2H⁺)²⁺); -UV (MeOH): λ (ε)=248 (15200), 318 (2300), 362 (7300), 384 (6600);

Example 3

General Instructions for the Phase-Transfer Catalytic Reaction of 2-Chloromethyl-1H-Phenalene-1-One with Alcohols 2-Chloromethyl-1H-phenalene-1-one (23 mg, 0.1 mmol) and a protected amino alcohol (0.4 mmol), as indicated in Examples 4a) and 5a) respectively, were dissolved in toluene (1 mL). Aqueous caustic soda solution (1 mL, 5 M, 5.0 mmol) was added, followed by tetrabutylammonium iodide (5 mg), and the batch was stirred vigorously for 20 h. It was diluted with 10 mL DCM, the aqueous phase was separated off and the organic phase was washed twice more with water (5 mL). After drying over MgSO₄, the solvent was drawn off and the residue purified by column chromatography with DCM/ethanol 40:1.

To deprotect the Boc group, the respectively obtained protected stage was dissolved in DCM (0.5 mL) and stirred with a saturated solution of HCl in diethyl ether (0.5 mL) for 2 h at room temperature. The product was then precipitated with diethyl ether, centrifuged and dried under reduced pressure.

Example 4a

[2-(1-Oxo-1H-phenalene-2-ylmethoxy)-ethyl]-carbamic acid-tert-butyl ester

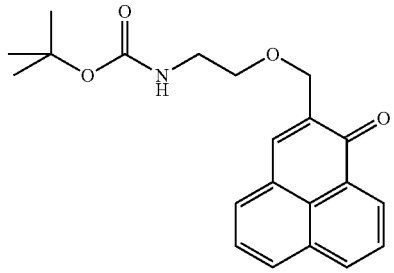 [SMILES: CC(C)(C)OC(=O)NCCOCC1=Cc2cccc3cccc(c23)C1=O]

(2-Hydroxy-ethyl)-carbamic acid-tert-butyl ester (64 mg, 0.4 mmol) was reacted as protected amino alcohol as indicated in Example 3). 32 mg of a tough yellow solid (0.091 mmol, 91% theoretical) was obtained.

$^1$H-NMR (300 MHz, CDCl$_3$): δ [ppm]=1.43 (s, 9H), 3.72 (d, 2H, J=6.4 Hz), 4.16 (d, 2H, J=6.4 Hz), 4.66 (s, 2H), 5.18 (bs, 1H), 7.62 (dd, 1H, J=7 Hz, 8 Hz), 7.76 (m, 2H), 7.93 (s, 1H), 8.05 (d, 1H, J=8 Hz), 8.22 (d, 1H, J=7.5 Hz), 8.62 (d, 1H, J=8 Hz); -MS (ESI-MS, CH$_2$Cl$_2$/MeOH+10 mmol NH$_4$OAc): e/z (%)=354.2 (100, MH$^+$), 298.2 (86, MH$^+$—C$_4$H$_9$), 254.1 (53, MH$^+$—CO$_2$—C$_4$H$_9$); -UV (MeOH): λ (ε)=247 (15100), 319 (2400), 361 (7200), 385 (6800);

Example 4b 2-((2-Aminoethoxy)methyl)-1H-phenalene-1-one hydrochloride

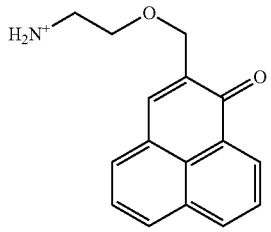 [SMILES: [NH3+]CCOCC1=Cc2cccc3cccc(c23)C1=O]

Of the protected stage obtained in Example 4a), 32 mg (0.09 mmol) was deprotected as indicated in Example 3). 25 mg of a yellow powder (0.086 mmol, 96% theoretical) was obtained.

$^1$H-NMR (300 MHz, MeOD): δ [ppm]=3.75 (m, 2H), 4.21 (m, 2H), 4.69 (s, 2H), 7.81 (dd, 1H, J=7 Hz, 8 Hz), 7.89 (m, 2H), 7.96 (s, 1H), 8.12 (d, 1H, J=8 Hz), 8.26 (d, 1H, J=7.5 Hz), 8.71 (d, 1H, J=8 Hz); -MS (ESI-MS, CH$_2$Cl$_2$/MeOH+10 mmol NH$_4$OAc): e/z (%)=254.1 (100, M$^+$); -UV (MeOH): λ (ε)=245 (15300), 318 (2200), 362 (7300), 383 (6800);

Example 5a

{2-[2-(1-Oxo-1H-phenalene-2-ylmethoxy)-ethoxy]-ethyl}-carbamic acid-tert-butyl ester

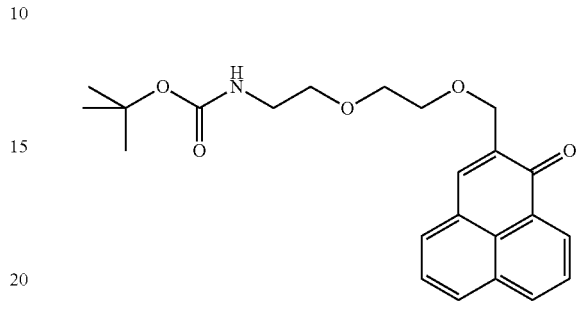

[2-(2-Hydroxy-ethoxy)-ethyl]-carbamic acid-tert-butyl ester (82 mg, 0.4 mmol) was reacted as protected amino alcohol as indicated in Example 3). 35 mg of a tough yellow solid (0.088 mmol, 88% theoretical) was obtained.

$^1$H-NMR (300 MHz, CDCl$_3$): δ [ppm]=1.42 (s, 9H), 3.11 (d, 2H, J=6.4 Hz), 3.32 (d, 2H, J=6.4 Hz), 3.54 (d, 2H, J=6.4 Hz), 4.09 (d, 2H, J=6.4 Hz), 4.64 (s, 2H), 5.14 (bs, 1H), 7.64 (dd, 1H, J=7 Hz, 8 Hz), 7.70 (m, 2H), 7.87 (s, 1H), 8.02 (d, 1H, J=8 Hz), 8.31 (d, 1H, J=7.5 Hz), 8.58 (d, 1H, J=8 Hz); -MS (ESI-MS, CH$_2$Cl$_2$/MeOH+10 mmol NH$_4$OAc): e/z (%)=398.2 (100, MH$^+$), 342.2 (71, MH$^+$—C$_4$H$_9$), 298.1 (46, MH$^+$—CO$_2$—C$_4$H$_9$); -UV (MeOH): λ (ε)=248 (15200), 317 (2300), 362 (7400), 383 (6600);

Example 5b 2-((2-(2-Aminoethoxy)ethoxy)methyl)-1H-phenalene-1-one hydrochloride

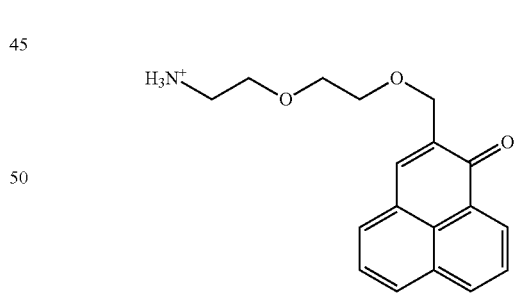

Of the protected stage obtained in Example 5a), 32 mg (0.08 mmol) was deprotected as indicated in Example 3). 23 mg of a yellow powder (84% theoretical; 0.067 mmol) was obtained.

$^1$H-NMR (300 MHz, MeOD): δ [ppm]=3.16 (m, 2H), 3.34 (d, 2H, J=6.4 Hz), 3.58 (d, 2H, J=6.4 Hz), 4.13 (d, 2H, J=6.4 Hz), 4.65 (s, 2H), 7.83 (dd, 1H, J=7 Hz, 8 Hz), 7.87 (m, 2H), 7.98 (s, 1H), 8.13 (d, 1H, J=8 Hz), 8.24 (d, 1H, J=7.5 Hz), 8.66 (d, 1H, J=8 Hz); -MS (ESI-MS, CH$_2$Cl$_2$/MeOH+10 mmol NH$_4$OAc): e/z (%)=298.1 (100, M$^+$); -UV (MeOH): λ (ε)=246 (15200), 316 (2200), 364 (7400), 386 (6800);

Example 6

Phase-Transfer Catalytic Reaction of 2-Chloromethyl-1H-Phenalene-1-One with Guanidines 2-Chloromethyl-1H-phenalene-1-one (23 mg, 0.1 mmol) and N,N',N''-tri-Boc-guanidine (144 mg, 0.4 mmol) were dissolved in toluene (1 mL). Aqueous caustic soda solution (1 mL, 5 M, 5.0 mmol) was added, followed by tetrabutylammonium iodide (5 mg), and the batch was stirred vigorously for 20 h. It was diluted with 10 mL DCM, the aqueous phase was separated off and the organic phase was washed twice more with water (5 mL). After drying over $MgSO_4$, the solvent was drawn off and the residue purified by column chromatography with DCM/ethanol 40:1.

To deprotect the Boc group, the pure product was dissolved in DCM (0.5 mL) and stirred with a saturated solution of HCl in diethyl ether (0.5 mL) for 2 h at room temperature. The product was then precipitated with diethyl ether, centrifuged and dried under reduced pressure.

Example 6a

N,N',N''-Tri(tert-butoxycarbonyl)-N-(1-oxo-1H-phenalene-2-ylmethyl)-guanidine

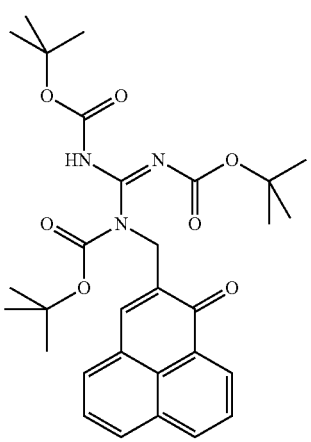 [SMILES: CC(C)(C)OC(=O)/N=C(/NC(=O)OC(C)(C)C)N(CC1=Cc2cccc3cccc(c23)C1=O)C(=O)OC(C)(C)C]

51 mg of a tough yellow solid (0.092 mmol, 92% theoretical) was obtained.

$^1$H-NMR (300 MHz, $CDCl_3$): δ [ppm]=1.41 (s, 9H), 1.43 (s, 9H), 1.44 (s, 9H), 4.62 (s, 2H), 7.65 (dd, 1H, J=7 Hz, 8 Hz), 7.78 (m, 2H), 7.91 (s, 1H), 8.02 (d, 1H, J=8 Hz), 8.17 (d, 1H, J=7.5 Hz), 8.67 (d, 1H, J=8 Hz); -MS (ESI-MS, $CH_2Cl_2$/MeOH+10 mmol $NH_4OAc$): e/z (%)=552.2 (100, $MH^+$), 496.2 (61, $MH^+$—$C_4H_9$), 452.1 (46, $MH^+$—$CO_2$—$C_4H_9$); -UV (MeOH): λ (ε)=246 (15200), 320 (2300), 360 (7300), 384 (6700);

Example 6b

N-(1-oxo-1H-phenalene-2-ylmethyl)-guanidine hydrochloride

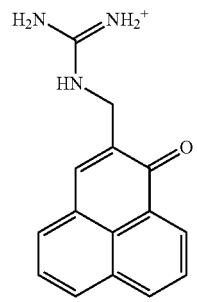

Of the protected stage obtained in Example 6a), 50 mg (0.09 mmol) was deprotected as indicated in Example 6). 26 mg of a yellow powder (0.091 mmol, 91% theoretical) was obtained.

$^1$H-NMR (300 MHz, MeOD): δ [ppm]=4.61 (s, 2H), 7.81 (dd, 1H, J=7 Hz, 8 Hz), 7.89 (m, 2H), 7.96 (s, 1H), 8.17 (d, 1H, J=8 Hz), 8.34 (d, 1H, J=7.5 Hz), 8.72 (d, 1H, J=8 Hz); -MS (ESI-MS, $CH_2Cl_2$/MeOH+10 mmol $NH_4OAc$): e/z (%)=452.1 (100, $M^+$); -UV (MeOH): λ (ε)=245 (15200), 321 (2300), 366 (7200), 385 (6700);

Example 7

Synthesis of 2-(4-pyridinyl)methyl)-1H-phenalene-1-one

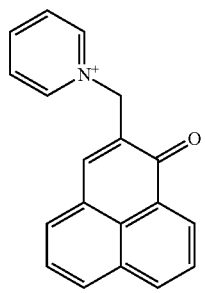 [SMILES: O=C1C(C[n+]2ccccc2)=Cc2cccc3cccc1c23]

Pyridine (316 µL, 4.0 mmol) was added to 2-chloromethyl-1H-phenalene-1-one (182 mg, 0.8 mmol) in ethanol (4.0 mL) and heating took place under reflux overnight at 80° C. After cooling, the solvent and excess pyridine were drawn off. For the further purification, the product was dissolved in DCM (0.5 mL) and precipitated with diethyl ether (10 mL). 230 mg of a pale yellow powder (0.749 mmol; 94% theoretical) was obtained.

HPLC: Gradient-elution in water [0.0059 wt.-% trifluoroacetic acid] (solution A) and acetonitrile [0.0059 wt.-% trifluoroacetic acid] (solution B). [t(min), % B]: (0, 5), (30, 98): Product peak at room temperature: 7.963 min; Purity: 95.8%

$^1$H-NMR (300 MHz, DMSO-d6): δ [ppm]=5.92 (s, 2H), 7.80 (dd, 1H, J=7 Hz, 8 Hz), 7.88 (dd, 1H, J=7.6 Hz, 8.5 Hz), 8.20 (m, 3H), 8.30 (d, 1H, J=7.6 Hz), 8.63 (m, 3H), 8.68 (d, 1H, J=8 Hz), 9.31 (m, 2H); -$^{13}$C-NMR (75 MHz, DMSO-d6): δ [ppm]=59.6 (−, 1C), 125.9 ($C_{quat}$, 1C), 126.5 ($C_{quat}$, 1C), 127.3 (+, 1C), 127.5 (+, 2C), 127.8 (+, 2C), 127.9 ($C_{quat}$, 1C), 130.4 (+, 1C), 131.5 ($C_{quat}$, 1C), 131.6 ($C_{quat}$, 1C), 133.4 (+, 1C), 133.9 (+, 1C), 136.1 (+, 1C), 144.1 (+, 1C), 145.3 (+, 1C), 145.8 (+, 1C), 171.9 ($C_{quat}$, 1C), 182.9 ($C_{quat}$, 1C); -MS (ESI-MS, $CH_2Cl_2$/MeOH+10 mmol $NH_4OAc$): e/z (%)=272.1 (100, $MH^+$); -UV (MeOH): λ (ε)=224 (21600), 248 (17400), 317 (2600), 363 (7200), 386 (6900);

Example 8

General Instructions for the Reaction of 2-Chloromethyl-1H-Phenalene-1-One with Amines 2-Chloromethyl-1H-phenalene-1-one (23 mg, 0.1 mmol) and an amine (0.4 mmol), as indicated in Examples 9) to 14) and 15a) to 19a) respectively, were dissolved in acetonitrile (1.0 mL) and potassium carbonate (70 mg, 0.5 mmol) were added and the batch is heated under reflux for 30 h at 80° C. After cooling, the solvent and all volatile components were drawn off.

In Examples 9) to 14), the end product was dissolved in DCM (0.5 mL) and precipitated with diethyl ether (10 mL).

In Examples 15a) to 19a), the residue was purified by column chromatography with DCM/ethanol 40:1.

Then, in Examples 15a) to 19a), to deprotect the Boc group in each case the protected stage was dissolved in DCM (0.5 mL) and stirred with a saturated solution of HCl in diethyl ether (0.5 mL) for 2 h at room temperature. The product was then precipitated with diethyl ether and centrifuged. For the further purification, the product was dissolved in DCM (0.5 mL) and precipitated again with diethyl ether (10 mL). Lastly, drying was carried out under reduced pressure.

Example 9

2-((N,N-Diethyl)aminomethyl)-1H-phenalene-1-one hydrochloride

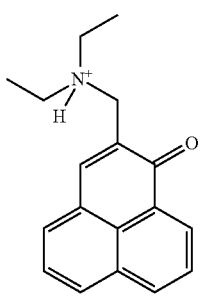 [SMILES: CC[NH+](CC)CC1=Cc2cccc3cccc(c23)C1=O]

Diethylamine (29 mg, 0.4 mmol) was reacted as amine as indicated in Example 8).

The obtained crude product was purified by column chromatography with DCM/EtOH 6:1 and protonated with HCl. 18 mg of a tough yellow solid (0.06 mmol; 60% theoretical) was obtained.

$^1$H-NMR (300 MHz, MeOD): δ [ppm]=1.42 (t, 6H, J=7.1 Hz), 3.14 (q, 4H, J=7.1 Hz), 4.68 (s, 2H), 7.87 (dd, 1H, J=7 Hz, 8 Hz), 7.81 (dd, 1H, J=7.6 Hz, 8.5 Hz), 8.10 (m, 1H), 8.26 (d, 1H, J=7.6 Hz), 8.62 (d, 1H, J=8 Hz), 9.31 (m, 2H); -MS (ESI-MS, $CH_2Cl_2$/MeOH+10 mmol $NH_4OAc$): e/z (%)=267.1 (100, $M^+$); -UV (MeOH): λ (ε)=246 (15100), 319 (2200), 365 (7100), 388 (6700);

Example 10

2-((N,N,N-Triethyl)aminomethyl)-1H-phenalene-1-one hydrochloride

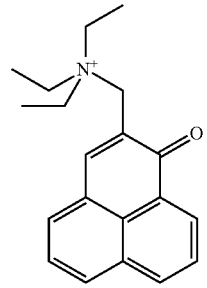 [SMILES: CC[N+](CC)(CC)CC1=Cc2cccc3cccc(c23)C1=O]

Triethylamine (40 mg, 0.4 mmol) was reacted as amine as indicated in Example 8). 24 mg of a tough yellow solid (0.076 mmol; 76% theoretical) was obtained.

$^1$H-NMR (300 MHz, $CDCl_3$): δ [ppm]=1.04 (t, 9H, J=7.1 Hz), 2.57 (q, 6H, J=7.1 Hz), 5.24 (s, 2H), 7.72 (dd, 1H, J=7 Hz, 8 Hz), 7.83 (dd, 1H, J=7.6 Hz, 8.5 Hz), 8.14 (m, 1H), 8.22 (d, 1H, J=7.6 Hz), 8.65 (d, 1H, J=8 Hz), 9.26 (m, 2H); -MS (ESI-MS, $CH_2Cl_2$/MeOH+10 mmol $NH_4OAc$): e/z (%)=295.1 (100, $M^+$); -UV (MeOH): λ (ε)=244 (15200), 319 (2200), 360 (7200), 384 (6700);

Example 11

2-{[Tris-(2-hydroxy-ethyl)-amino]-methyl}-phenalene-1-one hydrochloride

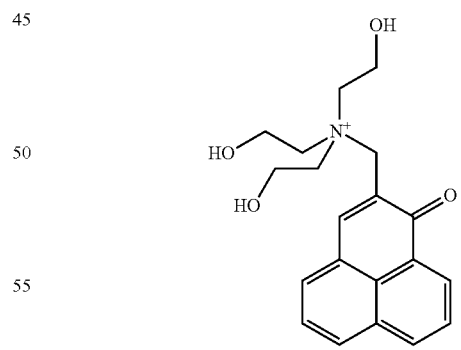

Triethanolamine (61 mg, 0.4 mmol) was reacted as amine as indicated in Example 8). 27 mg of a tough yellow solid (0.071 mmol; 71% theoretical) was obtained.

$^1$H-NMR (300 MHz, $CDCl_3$): δ [ppm]=2.54 (t, 6H, J=7.1 Hz), 3.66 (t, 6H, J=7.1 Hz), 3.76 (bs, 3H), 4.21 (s, 2H), 7.39 (dd, 1H, J=7 Hz, 8 Hz), 7.61 (dd, 1H, J=7.6 Hz, 8.5 Hz), 7.73 (m, 1H), 7.92 (d, 1H, J=7.6 Hz), 8.07 (d, 1H, J=8 Hz), 8.18 (m, 1H), 8.22 (m, 1H); -MS (ESI-MS, $CH_2Cl_2$/MeOH+10 mmol NH$_4$OAc): e/z (%)=343.1 (100, M$^+$); -UV (MeOH): λ (ε)=244 (15000), 320 (2300), 362 (7300), 386 (6800);

Example 12

2-Morpholin-4-ylmethyl-phenalene-1-one hydrochloride

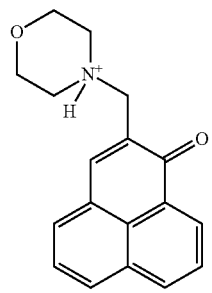 [SMILES: O=C1C(C[NH+]2CCOCC2)=Cc2cccc3cccc1c23]

Morpholine (34 mg, 0.4 mmol) was reacted as amine as indicated in Example 8). The crude product was purified by column chromatography with DCM/EtOH 6:1 and protonated with HCl. 18 mg of a tough yellow solid (0.081 mmol; 81% theoretical) was obtained.

$^1$H-NMR (300 MHz, CDCl$_3$): δ [ppm]=3.16 (m, 4H), 4.01 (m, 4H), 4.29 (s, 2H), 7.63 (dd, 1H, J=7 Hz, 8 Hz), 7.79 (m, 2H), 8.02 (d, 1H, J=8 Hz), 8.13 (m, 1H), 8.24 (dd, 1H, J=7.6 Hz, 8.5 Hz), 8.63 (d, 1H, J=8.5 Hz), 8.81 (s, 1H); -MS (ESI-MS, CH$_2$Cl$_2$/MeOH+10 mmol NH$_4$OAc): e/z (%)=281.1 (100, M$^+$); -UV (MeOH): λ (ε)=246 (15200), 322 (2200), 363 (7200), 384 (6700);

Example 13

2-(4-Methyl-piperazin-1-ylmethyl)-phenalene-1-one hydrochloride

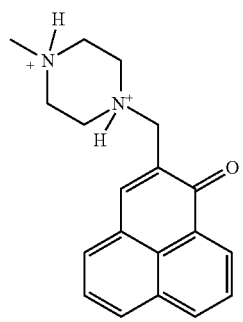

1-N-Methylpiperazine (29 mg, 0.4 mmol) was reacted as amine as indicated in Example 8). The crude product was purified by column chromatography with DCM/EtOH 6:1 and protonated with HCl. 24 mg of a yellow solid (0.064 mmol; 64% theoretical) was obtained.

$^1$H-NMR (300 MHz, CDCl$_3$): δ [ppm]=2.33 (s, 3H), 2.78 (m, 2H), 3.21 (m, 2H), 5.11 (s, 2H), 7.58 (dd, 1H, J=7 Hz, 8 Hz), 7.78 (m, 2H), 8.02 (m, 1H), 8.13 (d, 1H, J=8 Hz), 8.58 (dd, 1H, J=7.5 Hz, 8.5 Hz), 8.91 (m, 1H); -MS (ESI-MS, CH$_2$Cl$_2$/MeOH+10 mmol NH$_4$OAc): e/z (%)=294.1 (100, M$^+$); -UV (MeOH): λ (ε)=246 (15100), 318 (2200), 364 (7300), 388 (6700);

Example 14

2-(4-Dimethylamino-piperidin-1-ylmethyl)-phenalene-1-one hydrochloride

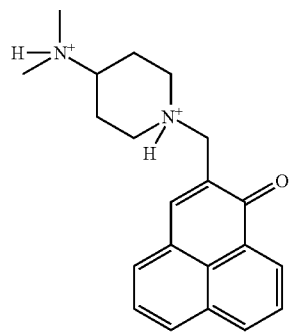 [SMILES: C[NH+](C)C1CC[NH+](CC2=Cc3cccc4cccc(c34)C2=O)CC1]

4-Dimethylaminopiperidine (42 mg, 0.4 mmol) was reacted as amine as indicated in Example 8). The crude product was purified by column chromatography with DCM/EtOH 6:1 and protonated with HCl. 25 mg of a yellow solid (0.067 mmol; 67% theoretical) was obtained.

$^1$H-NMR (300 MHz, CDCl$_3$): δ [ppm]=1.76 (m, 5H), 2.38 (s, 6H), 2.23 (m, 2H), 3.61 (m, 2H), 6.32 (s, 2H), 7.69 (dd, 1H, J=7 Hz, 8 Hz), 7.82 (dd, 1H, J=7.6 Hz, 8.5 Hz), 8.12 (d, 1H, J=8 Hz), 8.17 (d, 1H, J=8 Hz), 8.26 (d, 1H, J=7.5 Hz), 8.70 (d, 1H, J=8 Hz), 9.42 (s, 1H); -MS (ESI-MS, CH$_2$Cl$_2$/MeOH+10 mmol NH$_4$OAc): e/z (%)=322.1 (100, M$^+$); -UV (MeOH): λ (ε)=245 (15100), 319 (2400), 363 (7200), 386 (6800);

Example 15a ((2-tert-Butoxycarbonylamino-ethyl)-{2-[(1-oxo-1H-phenalene-2-ylmethyl)-amino]-ethyl}-amino)-acetic acid-tert-butyl ester

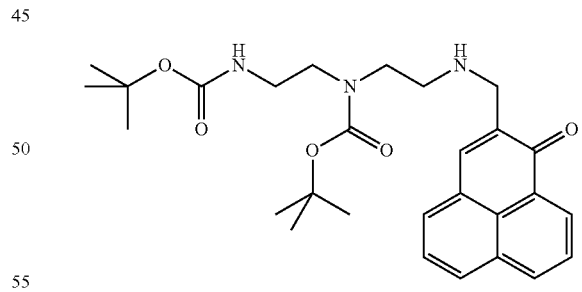

[(2-Amino-ethyl)-(2-tert-butoxycarbonylamino-ethyl)-amino]-acetic acid-tert-butyl ester (116 mg, 0.4 mmol) was reacted as amine as indicated in Example 8). 26 mg of a yellow, waxy solid (0.057 mmol; 57% theoretical) was obtained.

$^1$H-NMR (300 MHz, CDCl$_3$): δ [ppm]=1.41 (s, 9H), 1.43 (s, 9H), 2.93 (m, 2H), 3.21-3.58 (m, 8H), 3.91 (s, 2H), 5.58 (bs, 1H), 6.02 (bs, 1H), 7.58 (dd, 1H, J=7 Hz, 8 Hz), 7.81 (m, 3H), 8.01 (d, 1H, J=8 Hz), 8.22 (d, 1H, J=7.5 Hz), 8.62 (d, 1H, J=8 Hz); -MS (ESI-MS, CH$_2$Cl$_2$/MeOH+10 mmol NH$_4$OAc): e/z (%)=510.2 (100, MH$^+$), 454.2 (49, MH$^+$—

C₄H₉), 410.1 (21, MH⁺—CO₂—C₄H₉); -UV (MeOH): λ (ε)=245 (15200), 318 (2200), 362 (7300), 386 (6800);

Example 15b

2-{[2-(2-Amino-ethylamino)-ethylamino]-methyl}-phenalene-1-one hydrochloride

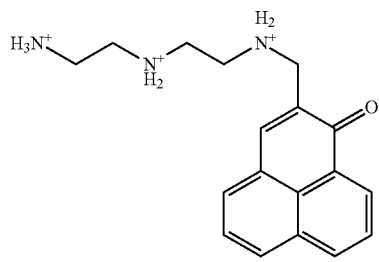

Of the protected stage obtained in Example 15a), 26 mg (0.05 mmol) was deprotected as indicated in Example 8). 17 mg of a yellow powder (0.045 mmol; 90% theoretical) was obtained.

¹H-NMR (300 MHz, MeOD): δ [ppm]=2.96 (m, 2H), 3.16-3.72 (m, 6H), 4.12 (s, 2H), 7.63 (dd, 1H, J=7 Hz, 8 Hz), 7.88 (m, 3H), 8.06 (d, 1H, J=8 Hz), 8.17 (d, 1H, J=7.5 Hz), 8.67 (d, 1H, J=8 Hz); -MS (ESI-MS, CH₂Cl₂/MeOH+10 mmol NH₄OAc): e/z (%)=310.1 (100, M⁺); -UV (MeOH): λ (ε)=242 (15400), 317 (2500), 361 (7100), 383 (6900);

Example 16a ([2-({2-[(2-tert-Butoxycarbonylamino-ethyl)-tert-butoxycarbonylmethyl-amino]-ethyl}-tert-butoxycarbonylmethyl-amino)-ethyl]-{2-[(1-oxo-1H-phenalene-2-ylmethyl)-amino]-ethyl}-amino)-acetic acid-tert-butyl ester

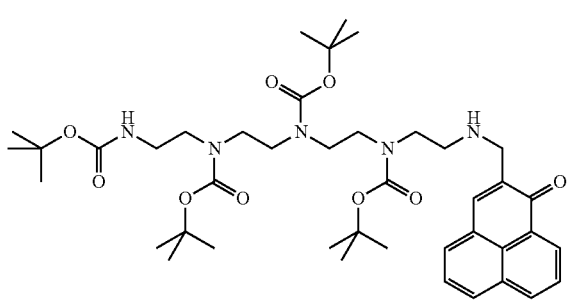 [SMILES: CC(C)(C)OC(=O)NCCN(CCN(CCN(CCNCC1=Cc2cccc3cccc(c23)C1=O)C(=O)OC(C)(C)C)C(=O)OC(C)(C)C)C(=O)OC(C)(C)C]

{(2-Amino-ethyl)-[2-({2-[(2-tert-butoxycarbonylamino-ethyl)-tert-butoxycarbonylmethyl-amino]-ethyl}-tert-butoxycarbonylmethyl-amino)-ethyl]-amino}-acetic acid-tert-butyl ester (240 mg, 0.4 mmol) was reacted as amine as indicated in Example 8). 33 mg of a tough yellow solid (39% theoretical; 0.039 mmol) was obtained.

¹H-NMR (300 MHz, CDCl₃): δ [ppm]=1.41 (s, 18H), 1.43 (s, 18H), 2.53 (m, 6H), 3.21-3.54 (m, 10H), 3.93 (s, 2H), 4.46 (bs, 1H), 5.02 (bs, 1H), 5.31 (bs, 1H), 5.74 (bs, 1H), 7.56 (dd, 1H, J=7 Hz, 8 Hz), 7.83 (m, 3H), 8.03 (d, 1H, J=8 Hz), 8.20 (d, 1H, J=7.5 Hz), 8.65 (d, 1H, J=8 Hz); -MS (ESI-MS, CH₂Cl₂/MeOH+10 mmol NH₄OAc): e/z (%)=823.2 (100, MH⁺), 767.2 (78, MH⁺—C₄H₉), 723.1 (13, MH⁺—CO₂—C₄H₉); -UV (MeOH): λ (ε)=2465 (15100), 322 (2400), 360 (7300), 384 (7000);

Example 16b

2-[(2-{2-[2-(2-Amino-ethylamino)-ethylamino]-ethylamino}-ethylamino)-methyl]-phenalene-1-one hydrochloride

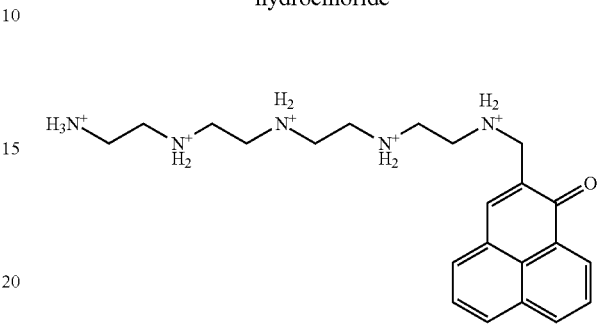

Of the protected stage obtained in Example 16a), 27 mg (0.033 mmol) was deprotected as indicated in Example 8). 17 mg of a yellow powder (0.029 mmol; 88% theoretical) was obtained.

¹H-NMR (300 MHz, MeOD): δ [ppm]=2.56 (m, 6H), 3.18-3.57 (m, 8H), 3.98 (s, 2H), 7.58 (dd, 1H, J=7 Hz, 8 Hz), 7.86 (m, 3H), 8.07 (d, 1H, J=8 Hz), 8.18 (d, 1H, J=7.5 Hz), 8.62 (d, 1H, J=8 Hz); -MS (ESI-MS, CH₂Cl₂/MeOH+10 mmol NH₄OAc): e/z (%)=386.1 (100, M⁺); -UV (MeOH): λ (ε)=245 (15500), 321 (2500), 361 (7200), 385 (6900);

Example 17a

N,N'-tert-Butoxycarbonyl-N"-{2-[(1-oxo-1H-phenalene-2-ylmethyl)-amino]-ethyl}-guanidine

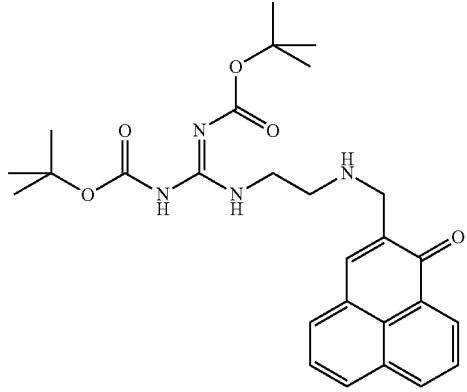 [SMILES: CC(C)(C)OC(=O)/N=C(\NCCNCC1=Cc2cccc3cccc(c23)C1=O)NC(=O)OC(C)(C)C]

N,N'-tert-Butoxycarbonyl-N"-(2-amino-ethyl)-guanidine (106 mg, 0.4 mmol) was reacted as amine as indicated in Example 8). 14 mg of a tough yellow solid (0.037 mmol; 37% theoretical) was obtained.

¹H-NMR (300 MHz, CDCl₃): δ [ppm]=1.42 (s, 18H), 2.62 (m, 2H), 3.38 (m, 2H), 4.63 (s, 2H), 7.58 (dd, 1H, J=7 Hz, 8 Hz), 7.78 (m, 2H), 7.94 (s, 1H), 8.03 (d, 1H, J=8 Hz), 8.18 (d, 1H, J=7.5 Hz), 8.63 (d, 1H, J=8 Hz); -MS (ESI-MS, CH₂Cl₂/MeOH+10 mmol NH₄OAc): e/z (%)=494.2 (100, MH⁺), 438.2 (62, MH⁺—C₄H₉), 394.1 (34, MH⁺—CO₂—C₄H₉); -UV (MeOH): λ (c)=244 (15100), 319 (2200), 360 (7200), 384 (6700);

Example 17b

N''-{2-[(1-Oxo-1H-phenalene-2-ylmethyl)-amino]-ethyl}-guanidine hydrochloride

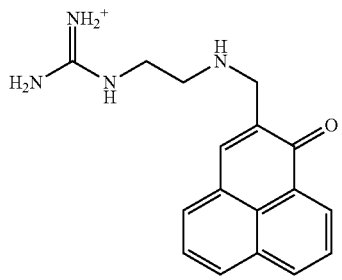 [SMILES: NC(=[NH2+])NCCNCC1=Cc2cccc3cccc(c23)C1=O]

Of the protected stage obtained in Example 17a), 12 mg (0.033 mmol) was deprotected as indicated in Example 8). 10 mg of a yellow powder (0.027 mmol; 81% theoretical) was obtained.

¹H-NMR (300 MHz, MeOD): δ [ppm]=2.64 (m, 2H), 3.42 (m, 2H), 4.62 (s, 2H), 7.56 (dd, 1H, J=7 Hz, 8 Hz), 7.82 (m, 2H), 7.91 (s, 1H), 8.05 (d, 1H, J=8 Hz), 8.21 (d, 1H, J=7.5 Hz), 8.61 (d, 1H, J=8 Hz); -MS (ESI-MS, CH₂Cl₂/MeOH+10 mmol NH₄OAc): e/z (%)=295.1 (100, M⁺); -UV (MeOH): λ (ε)=244 (15400), 321 (2200), 360 (7400), 386 (6800);

Example 18a

2-{[tris-(2-tert-Butoxycarbonyl-amino-ethyl)-amino]-methyl}-phenalene-1-one hydrochloride

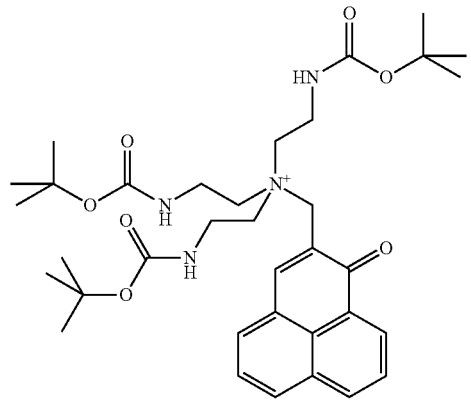 [SMILES: CC(C)(C)OC(=O)NCC[N+](CCNC(=O)OC(C)(C)C)(CCNC(=O)OC(C)(C)C)CC1=Cc2cccc3cccc(c23)C1=O]

tris-(2-tert-Butoxycarbonyl-amino-ethyl)-amine (164 mg, 0.4 mmol) was reacted as amine as indicated in Example 8). 48 mg of a yellow solid (0.073 mmol; 73% theoretical) was obtained.

¹H-NMR (300 MHz, CDCl₃): δ [ppm]=1.42 (s, 27H), 2.53 (m, 6H), 3.49 (m, 6H), 4.68 (s, 2H), 7.65 (dd, 1H, J=7 Hz), 7.77 (m, 3H), 8.03 (d, 1H, J=8 Hz), 8.21 (d, 1H, J=7.5 Hz), 8.61 (d, 1H, J=8 Hz); -MS (ESI-MS, CH₂Cl₂/MeOH+10 mmol NH₄OAc): e/z (%)=640.1 (100, MH⁺), 584.2 (67, MH⁺—C₄H₉), 540.1 (24, MH⁺—CO₂—C₄H₉); -UV (MeOH): λ (ε)=246 (15300), 316 (2300), 359 (7400), 388 (7100);

Example 18b

2-{[tris-(2-Amino-ethyl)-amino]-methyl}-phenalene-1-one hydrochloride

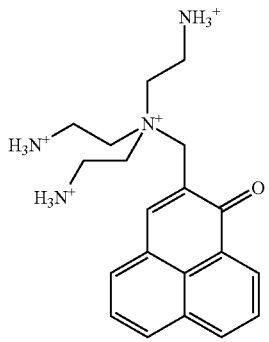 [SMILES: [NH3+]CC[N+](CC[NH3+])(CC[NH3+])CC1=Cc2cccc3cccc(c23)C1=O]

Of the protected stage obtained in Example 18a), 46 mg (0.07 mmol) was deprotected as indicated in Example 8). 30 mg of a yellow powder (89% theoretical; 0.062 mmol) was obtained.

¹H-NMR (300 MHz, MeOD): δ [ppm]=2.51 (m, 6H), 3.53 (m, 6H), 4.66 (s, 2H), 7.62 (dd, 1H, J=7 Hz, 8 Hz), 7.74 (m, 3H), 8.05 (d, 1H, J=8 Hz), 8.23 (d, 1H, J=7.5 Hz), 8.67 (d, 1H, J=8 Hz); -UV (MeOH): λ (ε)=246 (15500), 321 (2600), 360 (7200), 385 (6900);

Example 19a

2-{[tris-(2-(N,N'-tert-Butoxycarbonyl-guanidino)ethyl)-amino]-methyl}-phenalene-1-one hydrochloride

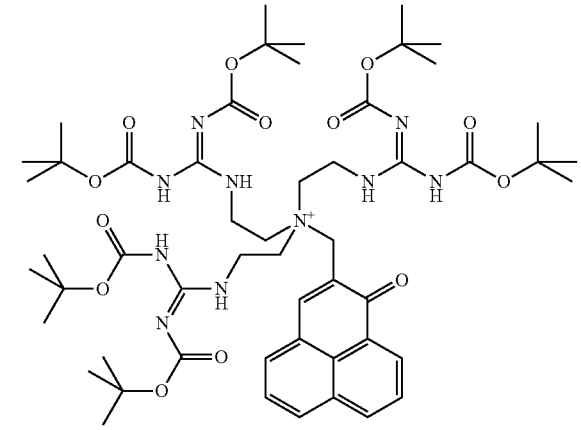 [SMILES: CC(C)(C)OC(=O)/N=C(\NCC[N+](CCN/C(=N\C(=O)OC(C)(C)C)NC(=O)OC(C)(C)C)(CCN/C(=N\C(=O)OC(C)(C)C)NC(=O)OC(C)(C)C)CC1=Cc2cccc3cccc(c23)C1=O)NC(=O)OC(C)(C)C]

tris-(2-(N,N'-tert-Butoxycarbonyl-guanidino)ethyl)-amine (330 mg, 0.4 mmol) was reacted as amine as indicated in Example 8). 81 mg of a tough yellow solid (78% theoretical; 0.078 mmol) was obtained.

¹H-NMR (300 MHz, CDCl₃): δ [ppm]=1.41 (s, 27H), 1.44 (s, 27H), 2.48 (m, 6H), 3.47 (m, 6H), 4.71 (s, 2H), 7.66 (dd, 1H, J=7 Hz, 8 Hz), 7.79 (m, 3H), 8.01 (d, 1H, J=8 Hz), 8.25 (d, 1H, J=7.5 Hz), 8.57 (d, 1H, J=8 Hz); -MS (ESI-MS, CH$_2$Cl$_2$/MeOH+10 mmol NH$_4$OAc): e/z (%)=1066.2 (100, MH$^+$), 1010.2 (58, MH$^+$—C$_4$H$_9$), 966.1 (37, MH$^+$—CO$_2$—C$_4$H$_9$); -UV (MeOH): λ (ε)=246 (15400), 319 (2500), 363 (7500), 384 (6900);

Example 19b

2-{[tris-(2-Guanidino-ethyl)-amino]-methyl}-phenalene-1-one hydrochloride

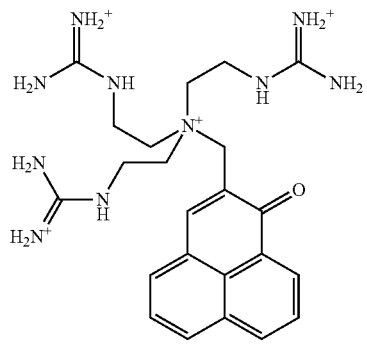 [SMILES: NC(=[NH2+])NCC[N+](CCNC(N)=[NH2+])(CCNC(N)=[NH2+])CC1=Cc2cccc3cccc(c23)C1=O]

Of the protected stage obtained in Example 19a), 73 mg (0.07 mmol) was deprotected as indicated in Example 8). 35 mg of a yellow powder (0.058 mmol; 83% theoretical) was obtained.

$^1$H-NMR (300 MHz, MeOD): δ [ppm]=2.56 (m, 6H), 3.53 (m, 6H), 4.66 (s, 2H), 7.68 (dd, 1H, J=7 Hz, 8 Hz), 7.84 (m, 3H), 8.04 (d, 1H, J=8 Hz), 8.22 (d, 1H, J=7.5 Hz), 8.60 (d, 1H, J=8 Hz); -UV (MeOH): λ (ε)=245 (15100), 317 (2200), 361 (7200), 385 (6900);

Example 20

Determination of the Photodynamic Activity Against Gram-Positive and Gram-Negative Bacteria Production of the Test Plates and Bacterial Strains A sample of the bacterial strain *Staphylococcus aureus* (ATCC number: 25923) or *Escherichia coli* (ATCC number: 25922) was extracted from a cryogenically frozen culture, isolated on Müller-Hinton agar plates, and cultured under aerobic conditions at 37° C. in an overnight culture. 10 ml Müller-Hinton liquid medium was then inoculated with a smear of the bacterial culture (individual colony) and incubated overnight at 37° C. The thus-obtained bacterial suspension was centrifuged for 15 min at 3000 rpm and the obtained bacterial pellet was resuspended in 10 ml sterile PBS. The optical density of the bacterial suspensions for the phototoxicity tests was OD$_{600nm}$=0.6, which corresponds to a bacterial count of ~8×10$^8$-10$^{12}$ bacteria per ml. The biochemical analysis and resistance determination of the bacteria were carried out with the VITEK2 system according to the guidelines M100-S14 of the NCCLS (National Committee for Clinical Laboratory Standards guidelines 2004).

For the sensitivity testing of medically significant pathogens to antibiotics and sulfonamides, according to the NCCLS guidelines, Müller-Hinton media with the following composition were used (Deutsche Gesellschaft für Hygiene und Mikrobiologie (DGHM, German Society for Hygiene and Microbiology), Institut für Hygiene und Mikrobiologie [Institute for Hygiene and Microbiology], University of Bonn, Germany):

a) Müller-Hinton broth (Oxoid, Wesel, Germany)
Contents: 2.0 g/l beef, dried infusion from 300 g, 17.5 g/l casein hydrolysate, 1.5 g/l starch, pH: 7.4+0.2 b) Müller-Hinton agar (Oxoid, Wesel, Germany)
Contents: see Müller-Hinton broth and 13 g/l agar-agar Performance of the Phototoxicity Test:

200 μl of a bacterial suspension (bacterial density: 10$^8$-10$^{12}$/ml) was incubated with 200 μl each of different concentrations of the photosensitizers listed in Table 1 at 37° C. in darkness for 15 minutes. The bacteria were then washed twice with PBS, resuspended in 200 μl PBS, the entire volume was transferred to a 96-well microtiter plate and then irradiated.

For the sensitization, the UV 236 lamp (emission 380-480 nm, with an emission maximum E$_{max}$: 418 nm) from Waldmann Medizintechnik was used and the plates lying on the light source were irradiated from below, in order to prevent scattering through the liquid. The applied light dose was 12.3 J/cm$^2$. As controls, bacterial suspensions that were irradiated, not irradiated and only incubated with photosensitizer were entrained, and incubated both with and without photosensitizer.

The CFU assay was then carried out to determine the colony-forming units per ml (CFU). For this, a series of dilutions from 10$^{-1}$ to 10$^{-9}$ of the corresponding bacterial suspension was produced. 100 μl was then plated onto Müller-Hinton plates and incubated at 37° C. for 24 h. The number of surviving colonies was then determined by counting and plotted on a graph as colony-forming units (CFU) per ml against the respectively used photosensitizer concentration.

Figure 2:
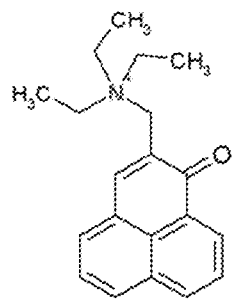
FIG. 2 shows the structural formula of the compound 2-((N,N,N-triethyl)aminomethyl)-1H-phenalene-1-one hydrochloride obtained in Example 10.
Figure 2:
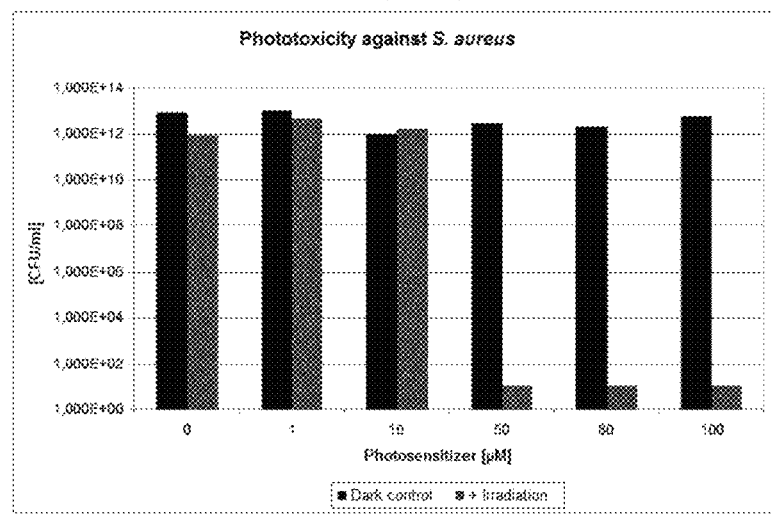
Figure 2:
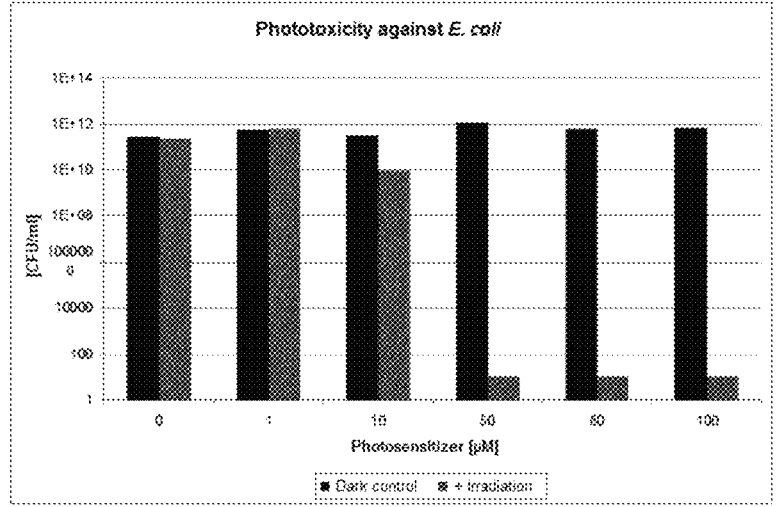
Figure 3:
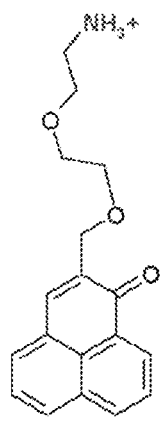
FIG. 3 shows the structural formula of the compound 2-((2-2-aminoethoxy) ethoxy)methyl)-1H-phenalene-1-one hydrochloride obtained in Example 5b).
Figure 3:
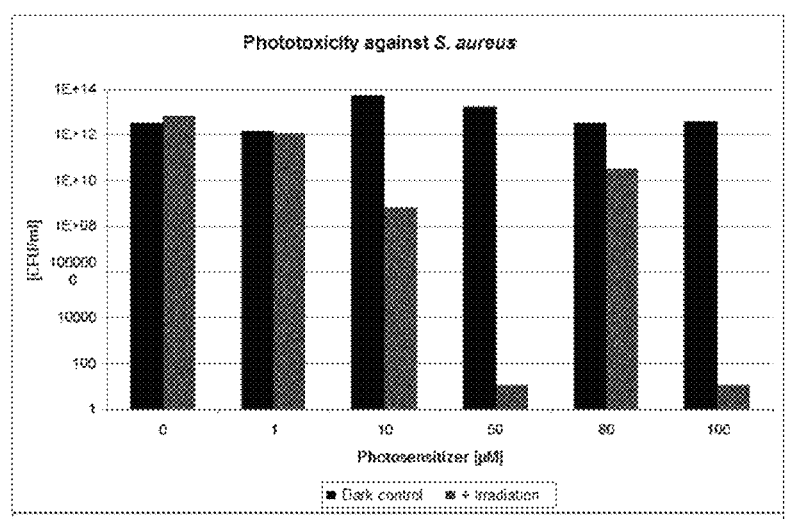
Figure 3:
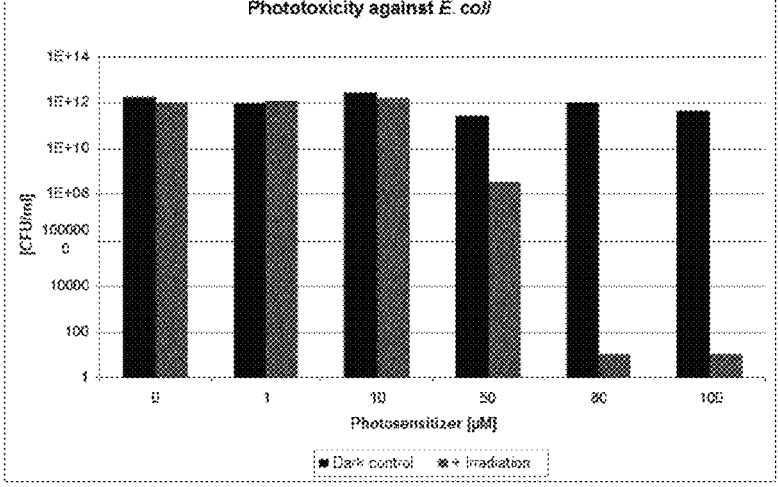
Figure 4:
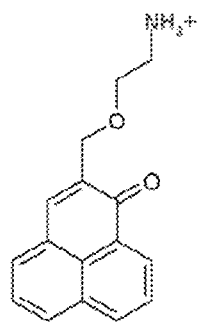
FIG. 4 shows the structural formula of the compound 2-((2-aminoethoxy)methyl)-1H-phenalene-1-one hydrochloride obtained in Example 4b).
Figure 4:
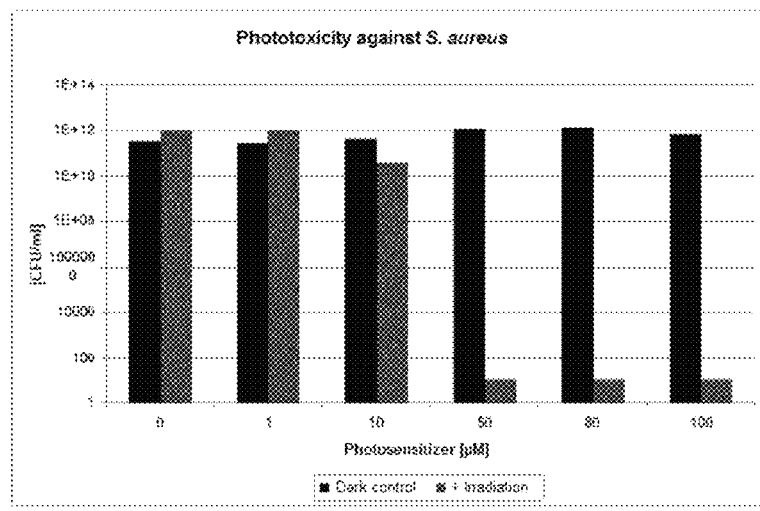
Figure 4:
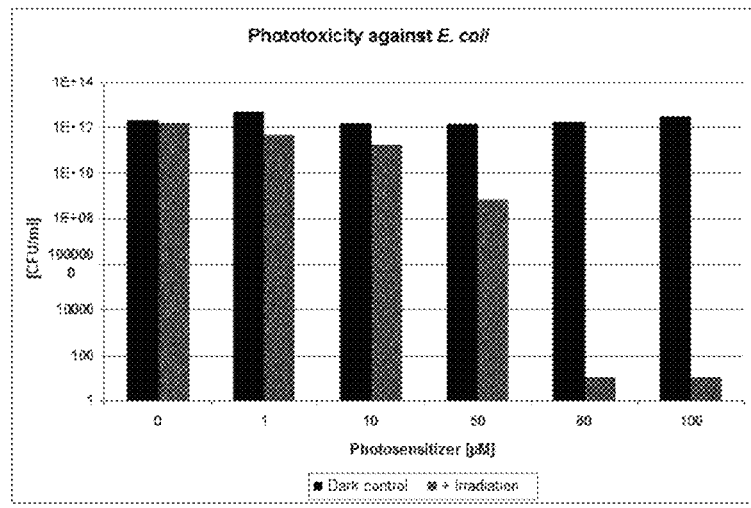
Figure 5:
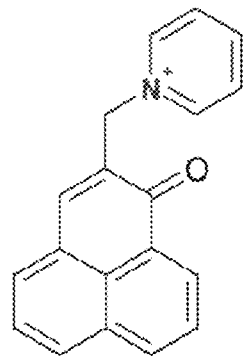
FIG. 5 shows the structural formula of the compound 2-((4-pyridinyl)methyl)-1H-phenalene-1-one obtained in Example 7.
Figure 5:
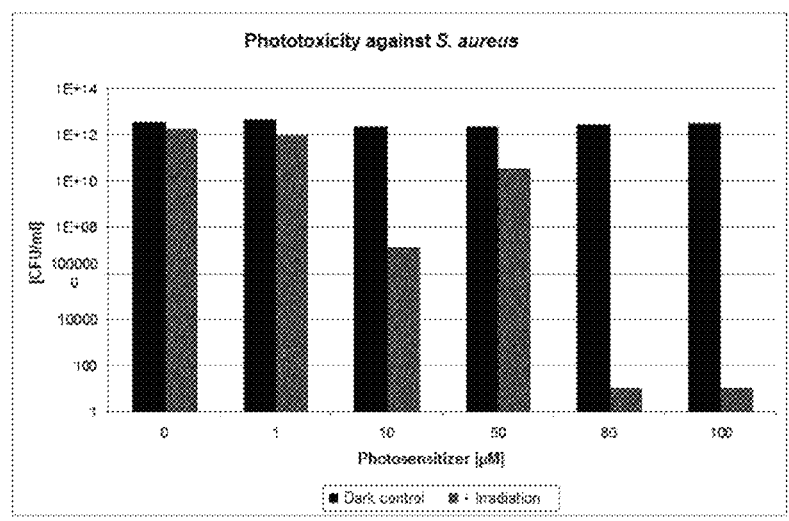
Figure 5:
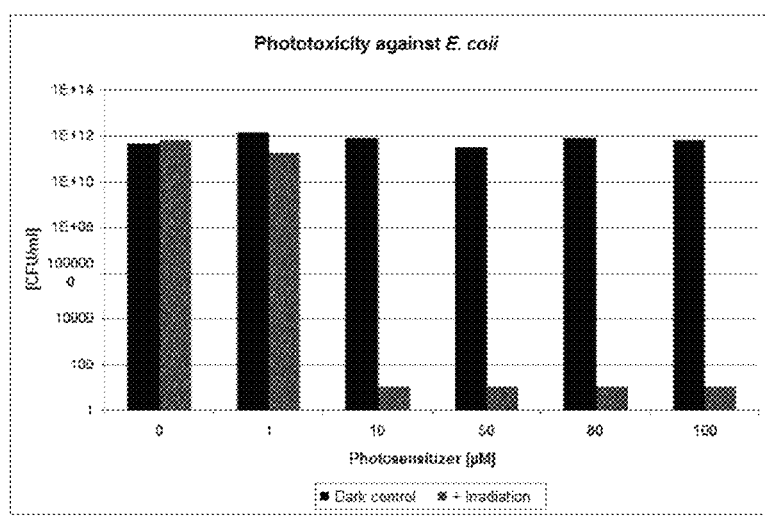

Result of the Phototoxicity Experiments:

The results of the phototoxicity experiments are represented in FIGS. 1 to 5. FIGS. 1 to 5 show the logarithmic decreases in the CFU/ml 24 hrs after irradiation as well as the associated controls (bacteria only irradiated; bacteria incubated with photosensitizer, but not irradiated; untreated bacteria) for the respectively used photosensitizer. As can be seen from FIGS. 1 to 5, an irradiation of the microorganisms used, *Staphylococcus aureus* (*S. aureus*) and *Escherichia coli* (*E. coli*), with a light dose of 12.3 J/cm$^2$ with blue light (E$_{max}$: 418 nm) for a period of 30 min in the absence of a photosensitizer has no influence on the number of surviving microorganisms compared with the non-illuminated control (grey bars: 0 μM photosensitizer=light control, only irradiated vs. black bars: 0 μM photosensitizer=pure bacteria without light and without photosensitizer).

In addition, the results represented in FIGS. 1 to 5 show that the incubation (15 min) of the respective photosensitizer with the microorganisms without subsequent exposure to light likewise has no influence on the number of surviving microorganisms (black bars: 1 μM, 10 μM, 50 μM, 80 μM and 100 μM=dark control, without irradiation vs. black bars: 0 μM=bacteria without photosensitizer and without irradiation).

As can be seen from FIGS. 1 to 5, a decrease in the CFU/ml occurs after incubation (15 min) of the microorganisms depending on the concentration used of the respective photosensitizers (1 μM, 10 μM, 50 μM, 80 μM and 100 μM) and subsequent irradiation with a light dose of 12.3 J/cm$^2$.

The effectiveness of the phototoxicity against bacteria after irradiation was established according to the following guidelines for hand hygiene in public health (Boyce, J. M., and D. Pittet. 2002. Guideline for Hand Hygiene in Health-Care Settings: recommendations of the Healthcare Infection Control Practices Advisory Committee and the HICPAC/SHEA/APIC/IDSA Hand Hygiene Task Force. Infect. Control. Hosp. Epidemiol. 23, pages 3-40):

reduction of the CFU/ml by 1 $\log_{10}$ step ≙ 90% effectiveness reduction of the CFU/ml by 3 $\log_{10}$ steps ≙ 99.9% effectiveness reduction of the CFU/ml by 5 $\log_{10}$ steps ≙ 99.999% effectiveness.

In order to have access for example to hygienic hand disinfection, a test product must lead to a reduction of the CFU/ml by at least 5 $\log_{10}$ steps (Gebel, J. 2002. Anforderungskatalog für die Aufnahme von chemischen Desinfektionsverfahren in die Desinfektionsmittel-Liste der DGHM. Desinfektionsmittel-Kommission der DGHM, pages 5-22.).

The decrease by ≥3 $\log_{10}$ steps can therefore be assumed as an effective inactivation, wherein *S. aureus* and *E. coli* were selected as examples of representatives from the group of gram-positive and gram-negative bacteria. The required concentration in order to achieve in each case a reduction by ≥3 $\log_{10}$ steps is represented in Table 1.

As can be seen from Table 1, the substances synthesized in Examples 2), 4b), 5b), 7) and 10) have an improved antimicrobial action compared with the starting substance perinaphthenone, because a lower concentration of these compounds is needed to achieve a reduction of the germ count by 3 $\log_{10}$ steps.

Compared with the starting substance perinaphthenone, an approximately 10-times lower concentration of the substances synthesized in Examples 2), 4b), 5b), 7) and 10) is needed to achieve a reduction by 3 $\log_{10}$ steps.

A reduction by 3 $\log_{10}$ steps corresponds in each case to a reduction of the colony-forming units by 99.9%.

TABLE 1

| | Photosensitizer | Required concentration in order to achieve a reduction by ≥ 3 $\log_{10}$ steps, |
|---|---|---|
| Comparison | 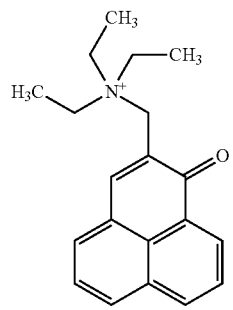 [SMILES: CC[N+](CC)(CC)CC1=Cc2cccc3cccc(c23)C1=O] | 200 µM for *S. aureus*; 300 µM for *E. coli* |
| Example 2) | 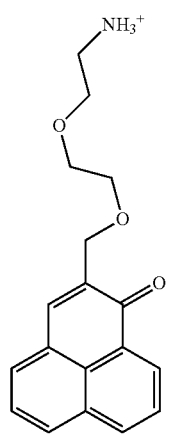 [SMILES: [NH3+]CCOCCOCC1=Cc2cccc3cccc(c23)C1=O] | 1 µM for *S. aureus*; 50 µM for *E. coli* |

TABLE 1-continued

| | Photosensitizer | Required concentration in order to achieve a reduction by ≥ 3 $\log_{10}$ steps, |
|---|---|---|
| Example 10) | 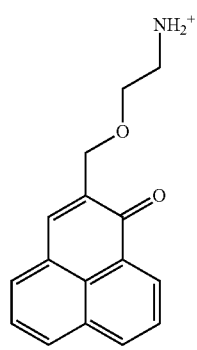 | 50 µM for *S. aureus*; 50 µM for *E. coli* |
| Example 5b) | | 50 µM for *S. aureus*; 80 µM for *E. coli* |
| Example 4b) | | 50 µM for *S. aureus*; 300 µM for *E. coli* |
| Example 7) | 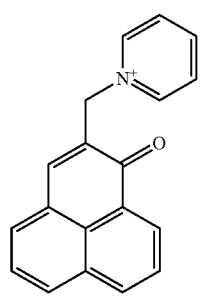 [SMILES: O=C1C(C[n+]2ccccc2)=Cc2cccc3cccc1c23] | 80 µM for *S. aureus*; 10 µM for *E. coli* |

Example 21

Use of Different 1H-Phenalene-1-One Derivatives for the Surface Disinfection of Catheter Tubes 5-cm long catheter sections were filled with 1 ml of a stable *S. aureus* solution (1 E+12 cfu/ml) and incubated overnight at 37° C. After drying-out of the solution, in each case 2 ml of a solution of PBS which contained a corresponding concentration (0, 1, 10, 50, 80 and 100 µM) of the compounds produced in Examples 2), 4b), 5b), 7) and 10) and 1H-phenalene-1-one was sprayed. After a short exposure time of 5 minutes in darkness, the catheter sections were illuminated with a light dose of 12.3 J/cm² with blue light ($E_{max}$: 418 nm) for a period of 30 min.

As a control, in each case non-illuminated catheter sections were used, to which the corresponding concentrations (0, 1, 10, 50, 80 and 100 µM) of the compounds produced in Examples 1b)-f) and 1H-phenalene-1-one were applied.

To determine the cell count, the illuminated and non-illuminated catheter sections were filled with 1 ml PBS and ultrasounded. Growth medium was added to the washing solution in different dilutions (10⁰ to 10⁷) and the solution was smeared onto agar plates. The cell count was performed after 24 h of incubation at 37° C.

Compared with the starting substance perinaphthenone, an approximately 10-times lower concentration of the substances synthesized in Examples 2), 4b), 5b), 7) and 10) is needed to achieve a reduction by 3 $\log_{10}$ steps.

What is claimed is:
1. Compound of Formula (1):

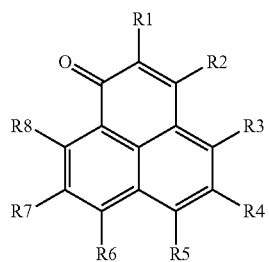
(1)

wherein R1 to R8, which can in each case independently of each other be the same or different, are in each case selected from the group consisting of hydrogen and the radical —(CH₂)ₖ—X, wherein k is an integer from 1 to 20, and wherein X is an organic radical which contains a) at least one neutral, protonatable nitrogen atom and/or b) at least one positively charged nitrogen atom, with the proviso that at least 1 radical R1 to R8 is —(CH₂)ₖ—X, and
wherein X means a radical of Formula (2):

(2)

wherein A is selected from the group consisting of an oxygen, a sulfur atom and a nitrogen atom which can be neutral or positively charged and wherein n is an integer from 1 to 8 and m is an integer from 0 to 100 and wherein B is a radical selected from the group consisting of Formula (3), Formula (4) and Formula (5):

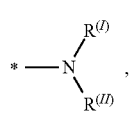
(3)

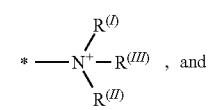
(4)

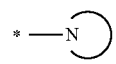
(5)

and wherein each of the radicals $R^{(I)}$, $R^{(II)}$ and $R^{(III)}$ independently of each other is selected from hydrogen or C1-C20 alkyl which can be straight-chained or branched and wherein the radical with Formula (5)

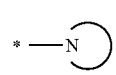
(5)

represents a substituted or unsubstituted heterocyclic radical with 5 to 7 ring atoms which comprise at least 1 carbon atom and 1 to 4 nitrogen atoms as well as optionally 1 or 2 oxygen or sulfur atoms, wherein the heterocyclic radical is saturated or unsaturated, or wherein X is a radical selected in each case from the group consisting of Formula 10, Formula 11, Formula 12, Formula 13, Formula 14, Formula 15, Formula 16, Formula 17, Formula 18, Formula 19, Formula 20, Formula 21, Formula 22, Formula 23, Formula 24, Formula 25, Formula 26, Formula 27, Formula 28, Formula 29, Formula 30, Formula 31, Formula 32 and Formula 33:

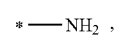
(10)

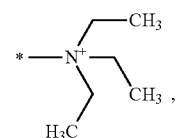
(11)

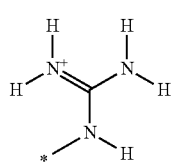
(12)

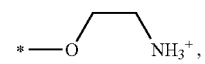
(13)

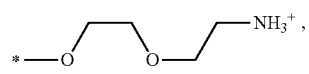
(14)

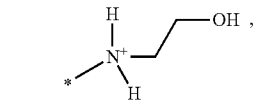
(15)

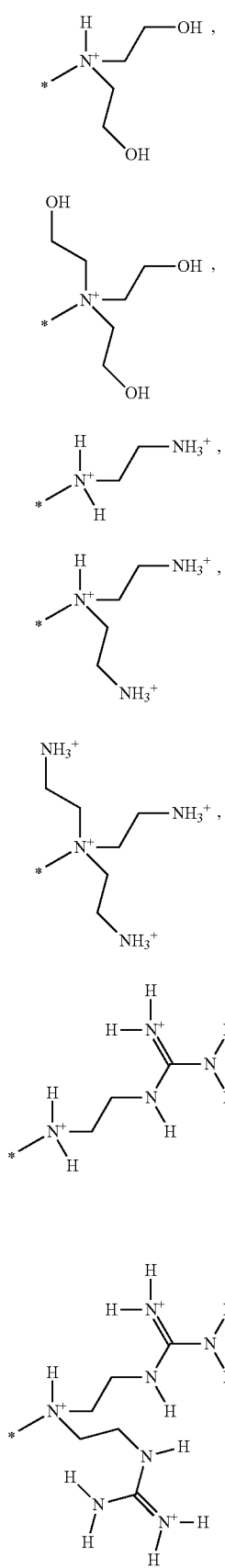
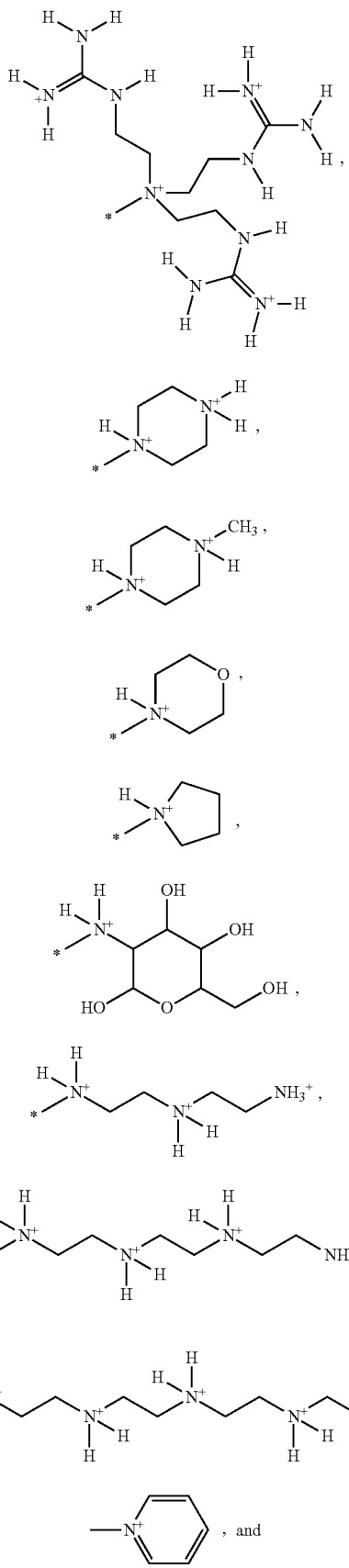

-continued

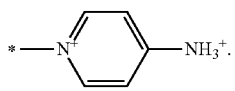 (33)

2. Compound according to claim 1, wherein R2 to R8 are hydrogen and wherein R1 means —(CH$_2$)$_k$—X, wherein k is an integer from 1 to 20 and wherein X is a radical selected from the group consisting of Formula 10, Formula 11, Formula 12, Formula 13, Formula 14, Formula 15, Formula 16, Formula 17, Formula 18, Formula 19, Formula 20, Formula 21, Formula 22, Formula 23, Formula 24, Formula 25, Formula 26, Formula 27, Formula 28, Formula 29, Formula 30, Formula 31, Formula 21 and Formula 33:

*—NH$_2$ , (10)

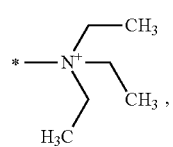 (11)

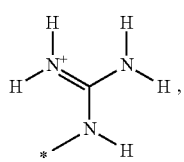 (12)

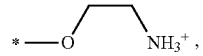 (13)

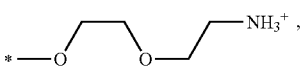 (14)

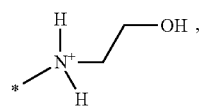 (15)

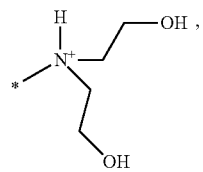 (16)

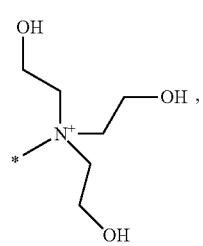 (17)

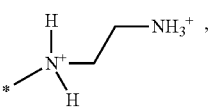 (18)

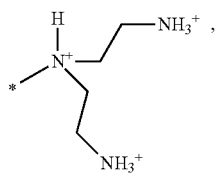 (19)

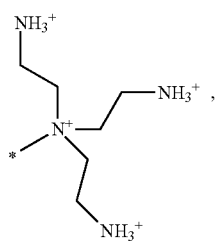 (20)

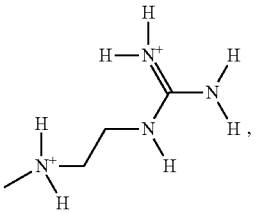 (21)

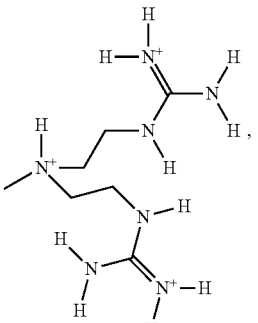 (22)

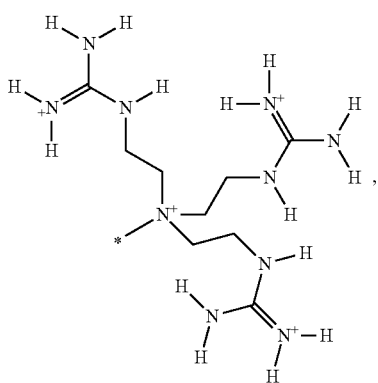 (23)

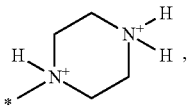 (24)

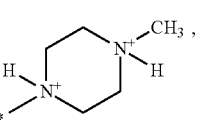 (25)

-continued

(26) 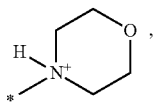

(27) 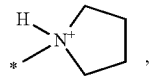

(28) 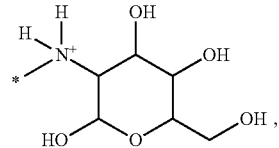

(29) 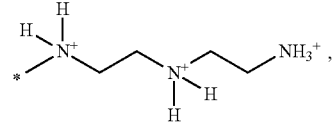

(30) 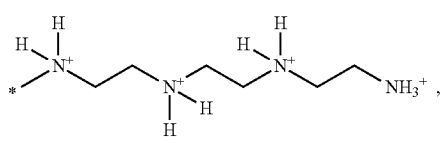

(31) 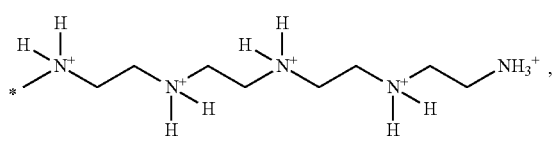

(32) 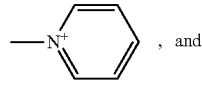, and

(33) 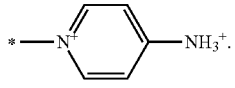.

3. A process for photodynamic inactivation of microorganisms located on or within a subject in need of such inactivation, said process comprising contacting said microorganisms with a compound according to claim 1 as a photosensitizer for inactivation of said microorganisms.

4. The process according to claim 3, wherein said microorganisms are selected from the group consisting of viruses, archaea, bacteria, bacterial spores, fungi, fungal spores, protozoa, algae and blood-transmissible parasites.

5. The process according to claim 3, wherein the compound is applied upon said subject in at least one selected from the group consisting of cleaning of teeth, dental prostheses and dental braces, treatment of a disease of the dental tissue and of the periodontium.

6. The process as claimed in claim 3, wherein said photosensitizer is applied upon said subject for treatment of an infectious skin disease.

7. A process for inactivating microorganisms located on or within an object, said process comprising applying to an object during at least one of surface cleaning and coating of said object, a compound according to claim 1.

8. The process as claimed in claim 7, wherein the object is selected from the group consisting of medical devices, food packaging and sanitary products.

9. Pharmaceutical composition containing at least one compound according to claim 1, a pharmacologically compatible salt, ester, or complex thereof, and a pharmaceutically acceptable carrier.

10. Coated object wherein a surface of the object has at least one compound according to claim 1.

11. Method for producing a compound according to claim 1, wherein the method comprises the following steps:
 (A1) reacting 1H-phenalene-1-one with at least one alkylating agent of the formula Y—(CH$_2$)$_h$—Z, wherein Y is selected from the group which consists of H, Cl, Br, I, p-toluene sulfonyl (OTs), methanesulfonyl (OMs), OH and alkyl$_2$S$^+$, wherein alkyl can be the same or independently of each other different, optionally in the presence of a catalyst, obtaining a compound with Formula (58):

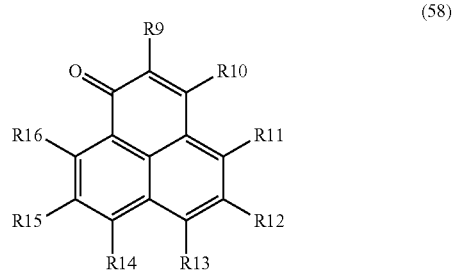

(58)

wherein R9 to R16, which can be the same or independently of each other different, mean in each case hydrogen or the radical —(CH$_2$)$_h$—Z, wherein h means an integer from 0 to 20, and wherein Z is selected from the group which consists of Cl, Br, I, p-toluene sulfonyl (OTs), methanesulfonyl (OMs), OH and alkyl$_2$S$^+$, wherein alkyl can be the same or independently of each other different and, with the proviso that at least 1 radical R9 to R16 is not hydrogen, or
 (A2) reacting 1H-phenalene-1-one with formaldehyde and at least one halogen hydracid, optionally in the presence of a catalyst, obtaining a compound with Formula (58):

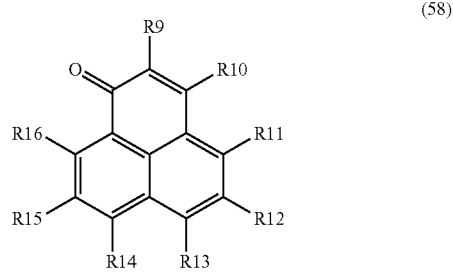

(58)

wherein R9 to R16, which can be the same or independently of each other different, mean in each case hydrogen or the radical —CH$_2$—W, and wherein W is selected from the group which consists of Cl, Br and I, with the proviso that at least 1 radical R9 to R16 is not hydrogen
 (B) reacting the compound obtained in step (A1) or (A2) with Formula (58) with an organic compound which contains a) at least one neutral, protonatable nitrogen atom and/or b) at least one positively charged nitrogen atom, optionally in the presence of a base, and optionally
 (C) removing any amino protecting groups present, obtaining the 1H-phenalene-1-one compound according to the invention of Formula (1).

12. The method according to claim 11, wherein the alkyl is selected from the group consisting of methyl, ethyl, propyl and butyl.

* * * * *